United States Patent
Steinmeyer et al.

(10) Patent No.: US 6,617,131 B2
(45) Date of Patent: Sep. 9, 2003

(54) NUCLEIC ACID MOLECULE ENCODING THE POTASSIUM CHANNEL PROTEIN, KCNQ5

(75) Inventors: Klaus Steinmeyer, Frankfurt (DE); Christian Lerche, Düsseldorf (DE); Constanze Scherer, Tübingen (DE); Guiscard Seebohm, Polle (DE); Andreas E. Busch, Kelkheim (DE)

(73) Assignee: Aventis Pharma Deutschland GmbH, Frankfurt (DE)

( * ) Notice: Subject to any disclaimer, the term of this patent is extended or adjusted under 35 U.S.C. 154(b) by 0 days.

(21) Appl. No.: 09/813,148

(22) Filed: Mar. 21, 2001

(65) Prior Publication Data

US 2002/0076809 A1 Jun. 20, 2002

Related U.S. Application Data

(60) Provisional application No. 60/194,041, filed on Apr. 3, 2000.

(30) Foreign Application Priority Data

Mar. 21, 2000 (DE) .......................... 100 13 732

(51) Int. Cl.$^7$ ............................. C07K 1/00; C07K 2/00; C07H 21/04; C12N 15/00; C12N 5/00
(52) U.S. Cl. ................ 435/69.1; 435/70.1; 435/243; 435/252.3; 435/320.1; 435/325; 530/350; 536/23.1; 536/23.5
(58) Field of Search ................ 435/69.1, 70.1, 435/243, 252.3, 320.1, 325, 252.5, 252.8, 255.2; 530/300, 350; 536/23.1, 23.5

(56) References Cited

FOREIGN PATENT DOCUMENTS

| | | |
|---|---|---|
| WO | WO 99/07832 A1 | 2/1999 |
| WO | WO 99/21875 A1 | 5/1999 |
| WO | WO 99/31232 A1 | 6/1999 |
| WO | WO 00/44786 A1 | 8/2000 |
| WO | WO 00/61606 A1 | 10/2000 |
| WO | WO 00/77035 A2 | 12/2000 |

OTHER PUBLICATIONS

Skolnick et al. From genes to protein structure and function: novel applications of computational approaches in the genomic era. Trends in Biotech 18(1): 34–39, 2000.*
Bork, A. Powers and pitfalls in sequence analysis: the 70% hurdle. Genome Res 10: 398–400, 2000.*
Doerks et al. Protein annotation: detective work for function prediction. Trends in Genetics 14(6): 248–250, 1998.*
Smith et al. The challenges of genome sequence annotation or "The devil is in the details". Nature Biotech 15: 1222–1223, 1997.*
Brenner, S.E. Errors in genome function. Trends in Genetics 15(4): 132–133, 1999.*
Bork et al. Go hunting in sequence databases but watch out for the traps. Trends in Genetics. 12(10): 425–427, 1996.*
Wells. J.A. Additivity of mutational effects in proteins. Biochemistry 29 (37): 8509–8517, 1990.*
Ngo et al. Computational complexity, protein structure prediction, and the Levinthal paradox. The Protein Folding Problem and Tertiary Structure Prediction, pp. 492–495, 1994.*
Lerche, C., et al; "Molecular Cloning and Functional Expression of KCNQ5, a Potassium Channel Subunit That May Contribute to Neuronal M–current Diversity"; The Journal of Biological Chemistry; Jul. 21, 2000; pp. 22395–22400; vol. 275; No. 29; The American Society for Biochemistry and Molecular Biology, Inc.; United States.
Schroeder, B., et al; "KCNQ5, a Novel Potassium Channel Broadly Expressed in Brain Mediates M–Type Currents"; The Journal of Biological Chemistry; Aug. 4, 2000; pp 24089–24095; vol. 275; No. 31; The American Society for Biochemistry and Molecular Biology, Inc.; United States.

* cited by examiner

Primary Examiner—Elizabeth Kemmerer
Assistant Examiner—Bridget E. Bunner
(74) Attorney, Agent, or Firm—Heller Ehrman White and McAuliffe

(57) ABSTRACT

KCNQ5, DNA encoding KCNQ5 or a polypeptide having KCNQ5 activity, related vectors, host cells and methods and a screening assay for identification of compounds which modify activity of a potassium channel KCNQ5 are described.

17 Claims, 6 Drawing Sheets

|  | KCNQ5 | KCNQ5/KCNQ3 | KCNQ2 | KCNQ2/KCNQ3 |
|---|---|---|---|---|
| activation, $\tau_{fast}$ | 116 ± 7 ms | 171 ± 6 ms * | 40 ± 6 ms | 73 ± 6 ms * |
| activation, $\tau_{slow}$ | 927 ± 51 ms | 897 ± 20 ms | 291 ± 71 ms | 490 ± 31 ms * |
| deactivation, $\tau_{fast}$ | 64 ± 5 ms | 42 ± 3 ms * | 29 ± 5 ms | 47 ± 3 ms * |
| deactivation, $\tau_{slow}$ | 269 ± 24 ms | 213 ± 38 ms | 241 ± 64 ms | 226 ± 29 ms |

NUCLEIC ACID MOLECULE ENCODING THE POTASSIUM CHANNEL PROTEIN, KCNQ5

This application claims priority to German Patent Application 10013732.6, filed Mar. 21, 2000, and U.S. provisional application No. 60/194,041, filed Apr. 3, 2000, which are hereby incorporated by reference, in their entirety.

FIELD OF THE INVENTION

The invention is related to a novel potassium channel protein KCNQ5 which is considered as a target for diseases of central nervous system and cardiovascular system. The protein is used as a screening tool for identification of compounds which improve symptoms of diseases of the central nervous system and cardiovascular system.

BACKGROUND OF THE INVENTION

Voltage-dependent potassium channels are key regulators of the resting membrane potential and modulate the excitability of electrically active cells like neurons and cardiac myocytes. Several classes of voltage-dependent $K^+$ channels have been cloned and probably all form oligomeric proteins through the assembly of four α-protein subunits. The tetrameric pore complex further can interact with auxiliary subunits that enhance and/or modify currents mediated by the pore-forming α-subunits.

The KCNQ family of voltage-dependent $K^+$ channels originally was established by positional cloning of the KCNQ1 gene (KvLQT1) which encodes a $K^+$ channel protein with six transmembrane domains and a characteristic pore region. So far the KCNQ family consists of four members all of which are associated with human diseases. KCNQ1 functionally interacts with KCNE1, a small β-subunit protein with a single transmembrane domain, to generate the slowly-activating delayed-rectifier $I_{Ks}$ current of cardiomyocytes. Inactivating mutations in both subunits result in the prolongation of the cardiac action potential and an increased risk of ventricular arrhythmias in patients with long QT-syndrome (LQTS). KCNQ1 and KCNE1 also are found in the inner ear and some loss of function mutations of KCNE1 and KCNQ1 are associated with hearing loss. In intestine, KCNQ1 probably associates with the structurally related KCNE3 protein to generate different $K^+$ channels. The KCNQ1/KCNE3 channel complex possibly represents the basolateral cAMP$^1$-regulated $K^+$ conductance in colonic crypts probably important for apical cAMP-stimulated chloride secretion and that is involved in secretory diarrhea and cystic fibrosis.

KCNQ2 and KCNQ3 are expressed in the brain and colocalize in various brain areas (Biervert, C. et al.; Science 279, 403–406, 1998). Whereas KCNQ2 generates $K^+$ currents very similar to KCNQ1 (Schröder, B. C. et al.; Nature 396, 687–690, 1998), KCNQ3 alone produces only small currents (Wang, W.-P. et al., J. Biol. Chem. 273, 19419–19423, 1998). Coexpression of both KCNQ2 and KCNQ3 resulted in currents that were at least 10-fold larger than that of KCNQ2 alone (Wang, H.-S. et al.; Science 282, 1890–1893, 1998), suggesting that KCNQ3 facilitates expression of KCNQ2 subunits, by formation of a heteromeric complex of KCNQ2 and KCNQ3 subunits. The genes encoding KCNQ2 and KCNQ3 have been cloned due to their linkage to a form of epilepsy in human infants and loss of function mutations have been identified in both genes in patients with benign familial neonatal convulsions (BNFC) (Sigh, N. A. et al.; N. Genet. 18, 25–29, 1998; Charlier, C. et al.; N. Genet. 18, 53–55, 1998)). Since epilepsy is due to an electrical hyperexcitability in the brain, KCNQs may have an important stabilizing role in the nervous system. Biophysical and pharmacological properties of KCNQ2/KCNQ3 currents are very similar to that of the native neuronal M-type $K^+$ current that is also characterized by muscarinic modulation and that is thought to be a prominent regulator of neuronal excitability as well. Similar to the native M-current, KCNQ2 KCNQ3 channel activity is strongly reduced by muscarinic acetylcholine agonists and therefore it is now assumed that KCNQ2 and KCNQ3 subunits contribute to the native M-channel.

KCNQ4, another member of this gene family, is expressed in sensory outer hair cells of the cochlea and is mutated in dominant deafness. Interestingly, coexpression of KCNQ3 with KCNQ4 also increased current amplitudes, although to a far less extent than observed with KCNQ2/KCNQ3 coexpression. This raises the possibility that different KCNQ channels can combine to produce variants of M-currents in different parts of the nervous system.

SUMMARY OF THE INVENTION

The object of the invention was to identify a gene coding for another member of the KCNQ family and the protein for use as a marker for treatment of various diseases. Compounds modifying the activity of KCNQ5 potassium channels may be useful in the treatment of some forms of epilepsy and other neurological or cardiovascular disorders.

In a first embodiment, an isolated nucleic acid molecule encoding a KCNQ5 polypeptide comprising SEQ ID NO:2 is provided. The invention further relates to an isolated nucleic acid molecule that is a nucleic acid sequence comprising SEQ ID NO:1. In another embodiment, the invention relates to a nucleic acid sequence that is at least 95% identical to SEQ ID NO:1, a nucleic acid sequence encoding SEQ ID NO:2; or a nucleic acid sequence that hybridizes under stringent conditions to one of the above; or a nucleic acid sequence that is complementary thereto.

In another embodiment, the invention provides an expression vector comprising an isolated nucleic acid molecule described above.

A further embodiment of the invention is a host cell, comprising the expression vector described above and a method of producing such a host cell.

The present invention also relates to an isolated polypeptide, with KCNQ5 activity, encoded by one of the above described nucleic acid molecules. Said protein may be produced by propagating a host cell harboring a recombinant vector including a DNA sequence encoding for an amino acid sequence or a polynucleotide sequence for KCNQ5 in a growth medium suitable either for bacteria or eucaryotic cells depending on the host cell type. These propagated cells are then harvested by common biochemical methods, such as centrifugation or filtration, and processed to obtain crude cell extracts. These cell extracts are purified by methods used for protein purification, such as size exchange chromatography, ion exchange chromatography, affinity chromatography and others, to retrieve the protein of interest (KCNQ5) separated from other compounds of the cell lysates.

In one embodiment, this isolated polypeptide comprising the amino acid sequence of SEQ ID NO:2 or a fragment thereof. The fragment generally contains at least about 10 consecutive amino acids and preferably about at least 30 to 50 consecutive amino acids.

In an additional embodiment, the isolated polypeptide of the invention comprises an amino acid sequence encoded by a polynucleotide that is SEQ ID NO:1. In another embodiment, the polypeptide of the invention is encoded by a nucleic acid sequence that is 95% identical to SEQ ID NO:1; or is a nucleic acid sequence that hybridizes under stringent conditions to one of the above, wherein the encoded polypeptide generates voltage-dependent, slowly activating K$^+$-selective currents that are insensitive to the K$^+$ channel blocker TEA and display a marked inward rectification at positive membrane voltages.

A further embodiment discloses a fusion protein comprising a polypeptide consisting of SEQ ID NO:2.

In an additional embodiment, this invention relates to an antibody that selectively binds KCNQ5. Further, the invention discloses a method of detecting a KCNQ5 polypeptide in a biological sample comprising contacting a detectably labeled antibody that selectively binds KCNQ5 with the biological sample and detecting the binding of the antibody with the KCNQ5 polypeptide in the biological sample.

In another embodiment, a cell culture for screening agonists and antagonists of KCNQ5 comprising cells that express KCNQ5 is disclosed. An example of such cells that express KCNQ5 are oocytes transformed with a nucleic acid molecule that transcribes SEQ ID NO:2.

A further embodiment of the invention is a method of screening for a compound that modifies the activity of KCNQ5. This modification may be, for example, inhibitory. In the method, a cell culture described above is provided, along with a compound to be screened. The compound may be a polypeptide, chemical compound, antibody, biological agent, antisense molecule, polynucleotide, oligopeptide, natural compound, or secondary metabolite. The activity of KCNQ5 without the compound is assessed by measuring K$^+$-selective currents from a single channel, single cell, or a membrane patch; or by measuring a signaling event, such as an ion flux. The compound is then added to the cell culture and incubated. The activity of KCNQ5 is then reassessed and compared to the activity without the compound to determine whether said compound modifies said activity of KCNQ5.

In an additional embodiment, a method of detecting a nucleic acid sequence encoding SEQ ID NO:2 in a biological sample comprising contacting a labeled nucleic acid probe that hybridizes with the nucleic acid sequence with the biological sample under conditions wherein the probe hybridizes with the nucleic acid sequence and detecting the hybridization of the probe to the nucleic acid sequence in the sample is provided.

In an additional embodiment, a kit comprising one or more containers, wherein at least one container contains a detectably labeled antibody that selectively binds a KCNQ5 polypeptide is provided. A kit comprising one or more containers, wherein at least one container contains a detectably labeled nucleic acid probe that hybridizes with a polynucleotide encoding SEQ ID NO:2 is also provided.

In a further embodiment, transgenic nonhuman animals having a transgene encoding KCNQ5 are also described.

DESCRIPTION OF FIGURES

Figure 1A:
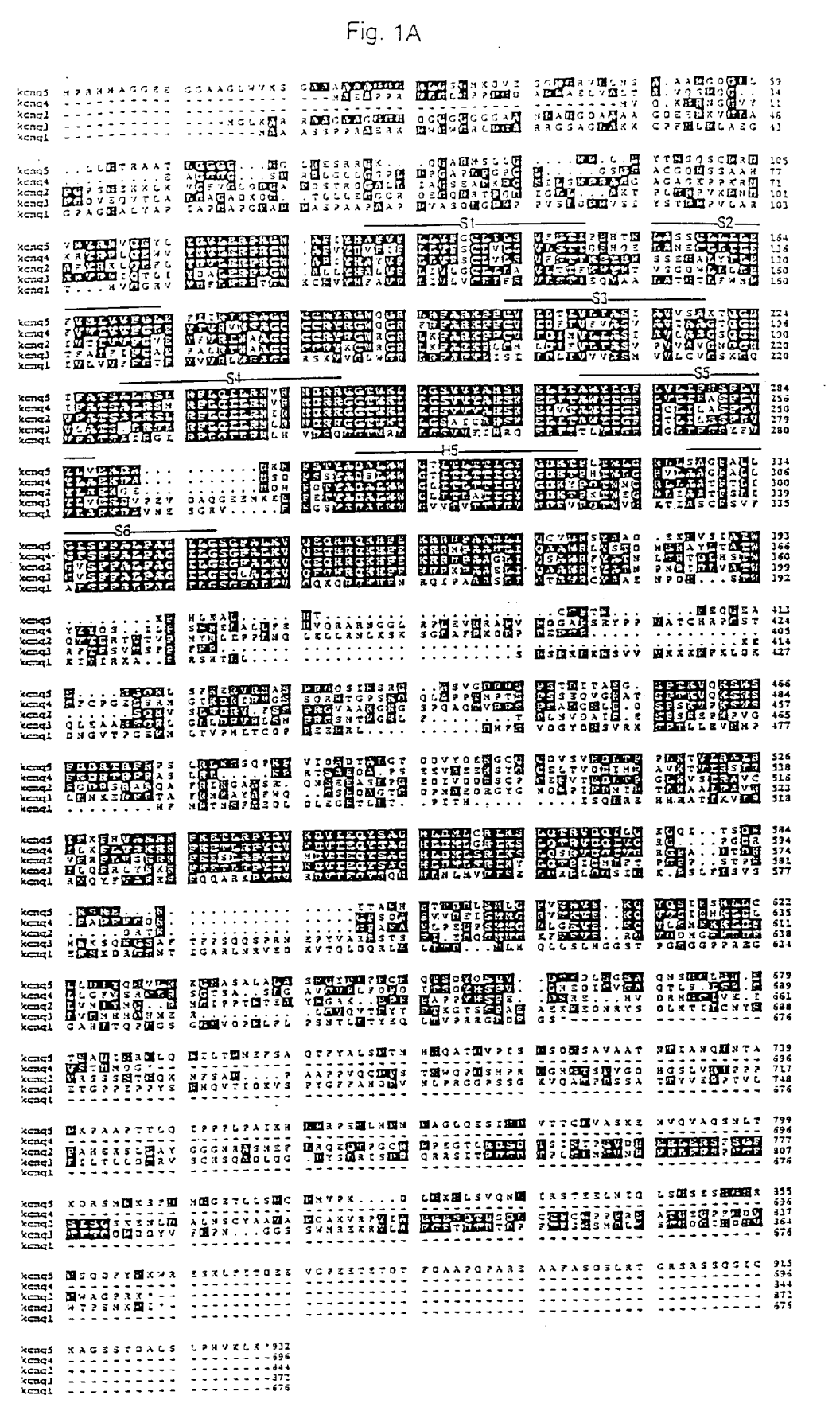

FIG. 1A: Shows the protein sequence of KCNQ5 (SEQ ID NO: 2) and comparison with other KCNQ proteins. A, alignment of human KCNQ5 with human KCNQ1 (SEQ ID NO: 3), KCNQ2 (SEQ ID NO: 4), KCNQ3 (SEQ ID NO: 5) and KCNQ4 (SEQ ID NO: 6). Identical and conserved amino acids are boxed in black and grey, respectively. The six putative transmembrane domains S1 through S6 and the pore region H5 are indicated by the stippled lines. The KCNQ5 sequence has been deposited in the EMBL/GenBank database.

FIG. 5: Shows the activation and Deactivation time constants of homomeric and heteromeric KCNQ channels. Oocytes were injected with 10 ng of either KCNQ5 or KCNQ2 cRNA, or with a mixture of 10 ng each of KCNQ5 and KCNQ3, or KCNQ2 and KCNQ3 cRNA. Currents were measured and fitted for activation and deactivation time constants as described in the text and in *Experimental Procedures*, respectively. Asterisks indicate significance. Values are mean±SEM (averaged from 9–16 oocytes).

DETAILED DESCRIPTION OF THE INVENTION

Figure 1B:
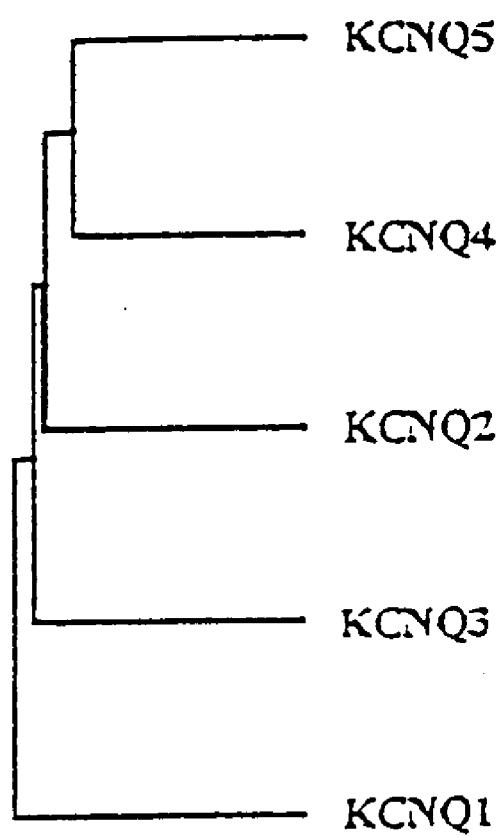
FIG. 1B: is a dendrogramm of the human KCNQ proteins, generated with the Pileup programm of the GCG software package.
Figure 2:
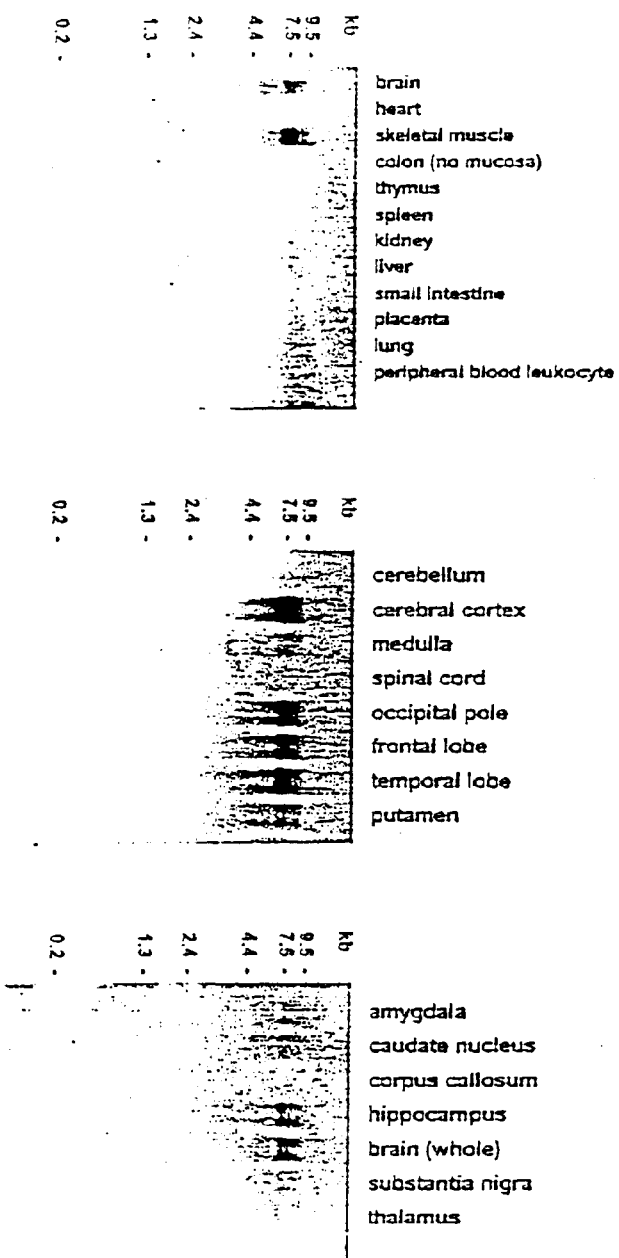
FIG. 2: Shows the tissue distribution of human potassium channel KCNQ5. A multiple tissue Northern blot and two blots from different parts of human brain containing poly (A)$^+$ RNA (Clontech) were hybridized with a KCNQ5-specific DIG-labeled RNA probe.

The abbreviations used are:
cAMP, cyclic 5′-adenosine monophosphate; DIG, digoxigenin; GCG, Genetics Computer Group, Wisconsin package version 10; I$_{ks}$, slow component of the cardiac delayed rectifier current; kb, kilobase; KCNQ, potassium channel of the KCNQ gene family; PHA, phytohemagglutinin; PKA, proteine kinase A; SEM, standard error of the mean; TEA, tetraethylammonium.

The problem of the invention was to identify another gene member of the KCNQ family including the protein for use as a target for treatment of various diseases.

KCNQ5 produces K$^+$ channels that are activated by depolarization and that are very similar to the currents generated by other KCNQ channels. KCNQ5 is expressed in skeletal muscle and in the brain, where its expression pattern overlaps with that of KCNQ 2 and KCNQ 3 that underlie the native M-current. Similar to KCNQ2, KCNQ5forms functional heteromers with KCNQ3, suggesting that neuronal M-channels probably can also include KCNQ5 subunits.

The subject matter of this invention is related to a DNA sequence coding for a polypeptide having KCNQ5 activity said polypeptide being selected from the following group:
a) a polypeptide having the amino acid sequence of a potassium channel KCNQ5,
b) a polypeptide having the amino acid sequence of SEQ ID No 2,
c) a polypeptide which in respect to b) is deficient in one or more amino acids or
d) a polypeptide which in respect to b) has one or more amino acids replaced.

This invention is further related to a DNA sequence wherein the DNA sequence has been selected from at least one of the following group of polynucleotide sequences:
a) a polynucleotide having the polynucleotide sequence of SEQ ID No 1,
b) a polynucleotide which hybridizes under stringent hybridization conditions to a polynucleotide sequence according to a),
c) a polynucleotide which hybridizes under low or medium stringency conditions to a polynucleotide sequence according to a), and
d) a polynucleotide sequence complementary to a polynucleotide sequence as defined in one of a), b), or c).

Thus, in one embodiment, the invention relates to an isolated nucleic acid molecule encoding a KCNQ5 polypeptide comprising SEQ ID NO:2. In another embodiment, the invention relates to an isolated nucleic acid molecule comprising SEQ ID NO:1, a nucleic acid molecule that is at least 95% identical to SEQ ID NO:1, a nucleic acid molecule that hybridizes under stringent conditions to one of the above or is complementary to one of the above.

The nucleic acid molecule of the present invention may be in the form of RNA, such as mRNA, or in the form of DNA, including, for instance cDNA and genomic DNA obtained by cloning or produced synthetically. The DNA may be double-stranded or single-stranded. Single stranded DNA or RNA may be the coding strand, also known as the sense strand, or it may be the non-coding strand, also referred to as the anti-sense strand.

By "isolated" nucleic acid molecule is intended a nucleic acid molecule, DNA or RNA, that has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules further includes such molecules produced synthetically.

In another embodiment, the DNA sequence as mentioned above can be part of the genome of each organism which harbors a gene for KCNQ5. In particular, the DNA sequence is part of a mammal or a human being. Preferred species amongst the mammals for the purpose of the invention are mouse and rat.

It is understood that all nucleic acid molecules encoding KCNQ5 are also included herein, as long as they encode a polypeptide with KCNQ5 activity. By "KCNQ5 activity" is meant the generation of voltage-dependent, slowly activating $K^+$-selective currents that are insensitive to the $K^+$ channel blocker TEA and display of a marked inward rectification at positive membrane voltages. Such activity may be assayed using well known techniques in the art. One such assay employs a two electrode voltage champ in cells, such as Xenopus Oocytes. Such nucleic acid molecules include naturally occurring, synthetic, and intentionally manipulated polynucleotides. For example, DNA encoding KCNQ5 may be subjected to site-directed mutagenesis. The nucleotide sequence for KCNQ5 also includes antisense sequences, and sequences encoding dominant negative forms of KCNQ5. The invention includes nucleotide sequences that are degenerate as a result of the genetic code. There are 20 natural amino acids, most of which are specified by more than one codon. Therefore, all degenerate nucleotide sequences are included in the invention as long as the amino acid sequence of KCNQ5 polypeptide encoded by the nucleotide sequence is functionally unchanged. When the sequence is RNA, the deoxynucleotides A, G, C, and T of SEQ ID NO:1 are replaced by ribonucleotides A, G, C, and U, respectively.

The present invention also includes fragments of the above described nucleic acid molecule. For instance, fragments include a segment of contiguous nucleotides of SEQ ID NO:1, which are at least about 15 bases, preferably about 20 bases or about 30 bases or 40 bases, or 50 bases in length. Such fragments are useful as diagnostic probes and PCR primers, as set forth herein. Of course, larger fragments of the nucleic acid molecules of the present invention also are contemplated. Fragments or portions of the polynucleotides of the present invention also may be used to synthesize full-length polynucleotides of the present invention.

For example, a nucleic acid probe may be used to identify a cDNA clone corresponding to a full length transcript and a genomic clone or clones that contain the complete gene of the present invention including regulatory and promoter regions, exons and introns. An example of a screen of this type comprises isolating the coding region of the gene by using the known DNA sequence to synthesize an oligonucleotide probe. Labeled oligonucleotides having a sequence complementary to that of the genes of the present invention are used to screen a library of human cDNA, genomic DNA or mRNA to determine which members of the library the probe hybridizes to.

In another embodiment, the invention relates to a nucleic acid molecule that hybridizes under stringent condition to SEQ ID NO:1.

In the present invention, "stringent" conditions means: washing of filters in 0.1×SSC, 0.1% SDS; 2 times for about 30 min. at about 65° C. (or about 5° C. below melting temperature). "Low medium" hybridization conditions means: washing of filters in 2×SSC, 0.1% SDS; 2 times for about 30 min. at about 65° C. (or about 10° C. below melting temperature).

The polynucleotides which hybridize to the above described polynucleotides in a preferred embodiment encode polypeptides which retain substantially the same biological function or activity as the mature polypeptide encoded by the cDNAs of SEQ ID NO:1. For example, such polypeptide could function as a soluble potassium channel by retaining the ability to bind the ligands for the receptor even though the polypeptide does not function as a membrane bound potassium channel, for example, by conducting passage of ions through the cell membrane. The same biological function or activity may be assessed as described above.

The nucleic acid molecule of the invention includes the DNA encoding SEQ ID NO:2 and conservative variations of SEQ ID NO:2. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The nucleic acid molecule of the present invention can be derived from any mammal, including rodents and primates. The preferred nucleic acid molecule is derived from humans. In the present invention, the nucleic acid molecule may be at least 95% identical to SEQ ID NO:1. One of skill in the art can determine the percentage of sequence identity between two sequences by aligning the encoded amino acid sequences, determining the corresponding alignment of the encoding polynucleotides, and then counting the number of residues shared between the sequences being compared at each aligned position. No penalty is imposed for the presence of insertions or deletions, but insertion or deletions are permitted only where required to accommodate an obviously increased number of amino acid residues in one of the sequences being aligned. Offsetting insertions just to improve sequence alignment are not permitted at either the polypeptide or polynucleotide level. Thus, any insertions in the polynucleotide sequence will have a length which is a multiple of 3. The percentage is given in terms of residues in the test sequence that are identical to residues in the comparison reference sequence.

Percent identity is calculated for oligonucleotides of this length by not allowing gaps in either the oligonucleotide or the polypeptide for purposes of alignment. Whenever at least one of two sequences being compared is a degenerate oligonucleotide comprising an ambiguous residue, the two sequences are identical if at least one of the alternative forms of the degenerate oligonucleotide is identical to the sequence with which it is being compared. As an illustration, AYAAA is 100% identical to ATAAA, since AYAAA is a mixture of ATAAA and ACAAA. Methods to determine the homology and percent identity of sequences are well known in the art. These methods can be performed manually (using mathematical calculations) or with a computer program, such as the Wisconsin package version 10.1-Unix (Genetics Computer Group (GCG), Madison, Wis.).

The invention refers further to a vector, preferably a recombinant DNA expression vector, said vector comprising a polynucleotide element which renders the vector suitable for its multiplication in procaryotic or eucaryotic cells and a DNA sequence as aforementioned coding for the amino acid sequence or a polynucleotide sequence for KCNQ5. The term "expression vector" refers to a plasmid, virus or other vehicle known in the art that has been manipulated by insertion or incorporation of the KCNQ5 genetic sequences. This DNA element which renders the vector suitable for multiplication can be an origin of replication which works in procaryotic or eucaryotic cells. An example for an origin of replication which works in procaryotic cells is the colE1 ori. A recombinant vector needs further a selection marker for control of growth of these organisms which harbor the vector. Suitable selection markers include genes which protect organisms from antibiotics (antibioticum resistance) e.g. ampicillin, streptomycin, chloramphenicol or provide growth under compound deprived environmental conditions (auxotrophic growth conditions) when expressed as proteins in cells. In a preferred embodiment of the invention for multiplication of the said recombinant vector the procaryotic cells are bacteria. In special preferred versions of the inventions the bacteria are in particular bacteria of *Escherichia coli* or of Bacillus spec. In a further preferred embodiment of the invention for the multiplication of the said recombinant vector the eucaryotic cells are cells of a cell line or yeast cells. In special preferred versions of the invention the cells of the cell line are cells of a COS, Hela-, or 3T3-cell-line and the yeast cells are cells of *Saccharomyces cerevisiae*.

Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Thus, the nucleic acid sequence which encodes KCNQ5 can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter. By "promoter" is meant minimal sequence sufficient to direct transcription. Thus, the said recombinant DNA of the present invention could provide for a promotor element which is operationally linked to a DNA sequence coding for the amino acid sequence or polynucleotide sequence of a KCNQ5 allowing transcription of the related RNA and/or expression of the related protein. Also included in the invention are those promoter elements which are sufficient to render promoter-dependent gene expression controllable for cell-type specific, tissue-specific, or inducible by external signals or agents; such elements may be located in the 5' or 3' regions of the gene. These promotor elements can be taken in preferred versions of the invention from procaryotic promoters or eucaryotic promoters. A procaryotic promoter is characterized by its ability to induce transcription in procaryotic organisms as a eucaryotic promoter is characterized by its ability to induce transcription in eucaryotic organisms. Both procaryotic and eucaryotic promoter elements can be preferred inducible promoters or further preferred constitutive promoters (see e.g., Bitter et al., Methods in Enzymology 153:516–544, 1987). An inducible promoter is switched on only when a signal event is present. The signal can be born by the organism's metabolism. Then it often consists of metabolic products, hormones, degradation products of macromolecules or other metabolic derived substances. The signal can also be provided by the environment. Then it may consist of radiation, temperature or chemical compounds of the environment. A constitutive promoter needs no induction for activity. When cloning in bacterial systems, inducible promoters such as pL of bacteriophage, gamma, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

The invention includes further a host cell and a cell culture comprised of said host cells. This host cell comprising at least one recombinant DNA vector as mentioned before.

"Host cells" are cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art. When the host cell is taken from procaryotic cells it preferably consists of a cell of a bacterium in particular of *Escherichia coli* or Bacillus spec. When this host cell consists of a eucaryotic cell it is preferred a cell of a cell line in particular a cell of a COS-, a Hela-, or 3T3-cell-line or a cell of a yeast in particular a cell of *Saccharomyces cerevisiae*.

This host cell can be produced by transforming the said host cell by a recombinant DNA vector comprising a DNA sequence coding for an amino acid sequence or polynucleotide sequence of a KCNQ5. The transformation can take place by routine methods used in microbiology as for example transformation of competent cells, $Ca^{2+}$-phosphate-precipitation or electroporation. By "transformation" is meant a genetic change induced in a cell following incorporation of new DNA (i.e., DNA exogenous to the cell). Where the cell is a mammalian cell, the genetic change is generally achieved by introduction of the DNA into the genome of the cell (i.e., stable).

By "transformed cell" is meant a cell into which (or into an ancestor of which) has been introduced, by means of recombinant DNA techniques, a DNA molecule encoding KCNQ5. Transformation of a host cell with recombinant DNA may be carried out by conventional techniques as are well known to those skilled in the art. Where the host is prokaryotic, such as *E. coli,* competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the KCNQ5 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Eukaryotic Viral Vectors, Cold Spring Harbor Laboratory, Gluzman ed., 1982).

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, such methods are well know to those skilled in the art.

Isolation and purification of microbial expressed polypeptide, or fragments thereof, provided by the invention, may be carried out by conventional means including preparative chromatography and immunological separations involving monoclonal or polyclonal antibodies.

The KCNQ5 polypeptides can be recovered and purified from recombinant host cells and cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. Protein refolding steps can be used, as necessary, in completing configuration of the mature protein. Finally, high performance liquid chromatography (HPLC) can be employed for final purification steps.

In one embodiment, the invention provides substantially purified KCNQ5 polypeptide. Preferably, KCNQ5 has an amino acid sequence set forth in SEQ ID NO:2. The term "substantially purified" as used herein refers to a polypeptide which is substantially free of other proteins, lipids, carbohydrates or other materials with which it is naturally associated. One skilled in the art can purify KCNQ5 using standard techniques for protein purification. The substantially pure polypeptide will yield a single major band on a non-reducing polyacrylamide gel. The purity of the KCNQ5 polypeptide can also be determined by amino-terminal amino acid sequence analysis.

As explained above, the invention refers also to a protein encoded by one of the DNA sequences as aforementioned. This protein has activity of a KCNQ5. Activity of KCNQ5 is characterized by ion transport of this transporter type, specifically, the generation of voltage-dependent, slowly activating $K^+$-selective currents that are insensitive to the $K^+$ channel blocker TEA and display of a marked inward rectification at positive membrane voltages. This activity was characterized in a two electrode voltage champ in Xenopus Oocytes. As described above, further included is production of a protein wherein first a host cell harboring a recombinant vector including a DNA sequence encoding for an amino acid sequence or a polynucleotide sequence for KCNQ5 is propagated in a suitable growth medium chosen from either media for bacteria or eucaryotic cells depending on the related host cell type. These propagated cells are second harvested by common methods of biochemistry as centrifugation or filtration and processed to obtain crude cell extracts. These cell extracts third are purified subsequently by methods used for protein purification as size exchange chromatography, ion exchange chromatography, affinity chromatography and others to gain the protein of interest (KCNQ5) separated from other compounds of the cell lysates.

The polypeptide of the invention may be expressed in a modified form, such as a fusion protein and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent storage and handling. Also, peptide moieties may be added to the polypeptide to improve purification. Such regions may be removed prior to final preparation of the peptide. Additionally, the fusion protein of the invention could include amino acids of other members of the KCNQ family.

In one embodiment, the polypeptide of the present invention comprises the amino acid sequence of SEQ ID NO:2 and is encoded by the nucleotide sequence of SEQ ID NO:1. However, the polypeptide of the invention can be varied without significant effect on the structure or function of the molecule.

Minor modifications of the KCNQ5 primary amino acid sequences may result in proteins which have substantially equivalent activity as compared to the unmodified counterpart polypeptide described herein. Such modifications may be deliberate, as by site-directed mutagenesis, or may be spontaneous. All of the polypeptides produced by these modifications are included herein as long as the biological activity of the KCNQ5 still exists.

The polypeptide of the present invention also includes fragments and variants of SEQ ID NO:2. "Variant" when referring to the polypeptide of SEQ ID NO:2, means polypeptides which retain essentially the same biological function or activity as a polypeptide comprising the full length SEQ ID NO:2. Such biological activity may be assessed in a two electrode voltage champ in a cell, such as a Xenopus oocyte.

A "fragment" is a segment of SEQ ID NO:2 that comprises contiguous amino acids.

The variant of the polypeptide SEQ ID NO:2 may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptides are fused with another compound, such as a compound to increase the half-life of the polypeptide (for example, polyethylene glycol), or (iv) one in which the additional amino acids are fused to the mature polypeptides. Such variants are deemed to be within the scope of those skilled in the art from the teachings herein.

The polypeptides of the present invention include the polypeptide of SEQ ID NO:2 as well as polypeptides which have at least 70% similarity to the polypeptide of SEQ ID NO:2 and more preferably at least a 90% similarity to the polypeptide of SEQ ID NO:2 and still more preferably at least a 95% similarity to the polypeptide of SEQ ID NO:2 and also includes fragments of such polypeptides with such portion of the polypeptide generally containing about at least 10 consecutive amino acids and preferably about at least 30 to 50 consecutive amino acids.

As known in the art "similarity" between two polypeptides is determined by comparing the amino acid sequence and its conserved amino acid substitutes of one polypeptide to the sequence of a second polypeptide. This can be done manually (using mathematical calculations) or with a computer program, such as the Wisconsin package version 10.1-Unix (Genetics Computer Group (GCG), Madison, Wis.).

Fragments or portions of the polypeptides of the present invention may be employed for producing the corresponding full-length polypeptide by peptide synthesis, therefore, the fragments may be employed as intermediates for producing the full-length polypeptides. Fragments also may be used to generate antibodies, as described below.

Antibodies

In another embodiment of the invention, the KCNQ5 polypeptides of the invention, including fragments thereof, can be used to produce antibodies which are immunoreactive or bind to epitopes of the KCNQ5 polypeptides. Polyclonal antibodies and antibodies which consist essentially of pooled monoclonal antibodies with different epitopic specificities, as well as distinct monoclonal antibody preparations are encompassed by the invention.

The preparation of polyclonal antibodies is well-known to those skilled in the art. See, for example, Green et at., "Production of Polyclonal Antisera," in: Immunochemical Protocols pages 1–5, Manson, ed., Humana Press 1992; Coligan et al., "Production of Polyclonal Antisera in Rabbits, Rats, Mice and Hamsters," in: Current Protocols in Immunology, section 2.4.1, 1992, which are hereby incorporated by reference.

The preparation of monoclonal antibodies likewise is conventional. See, for example, Kohler & Milstein, Nature 256:495, 1975; Coligan et al., sections 2.5.1–2.6.7; and Harlow et al., in: Antibodies: a Laboratory Manual, page 726, Cold Spring Harbor Pub., 1988, which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes et al., "Purification of Immunoglobulin G (IgG)," in: Methods in Molecular Biology, Vol. 10, pages 79–104, Humana Press, 1992.

Methods of in vitro and in vivo multiplication of monoclonal antibodies are well known to those skilled in the art. Multiplication in vitro may be carried out in suitable culture media is such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Therapeutic applications for antibodies disclosed herein are also part of the present invention. For example, antibodies of the present invention may also be derived from subhuman primate antibody. General techniques for raising therapeutically useful antibodies in baboons can be found, for example, in Goldenberg et al., International Patent Publication WO 91/11465, 1991, and Losman et al., Int. J. Cancer 46:310, 1990, which are hereby incorporated by reference.

Alternatively, a therapeutically useful anti-KCNQ5 antibody may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., Proc. Natl. Acad. Sci. USA 86:3833, 1989, which is hereby incorporated in its entirety by reference. Techniques for producing humanized monoclonal antibodies are described, for example, by Jones et al., Nature 321:522, 1986; Riechmann et al., Nature 332:323, 1988; Verhoeyen et al., Science 239:1534, 1988; Carter et al., Proc. Nat'l Acad. Sci. USA 89:4285, 1992; Sandhu, Crit. Rev. Biotech. 12:437, 1992; and Singer et al., J. Immunol. 150:2844, 1993, which are hereby incorporated by reference.

Antibodies of the invention also may be derived from human antibody fragments isolated from a combinatorial immunoglobulin library. See, for example, Barbas et al., in: Methods: a Companion to Methods in Enzymology, Vol. 2, page 119, 1991; Winter et al., Ann. Rev. Immunol. 12:433, 1994, which are hereby incorporated by reference. Cloning and expression vectors that are useful for producing a human immunoglobulin phage library can be obtained, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13, 1994; Lonberg et al., Nature 368:856, 1994; and Taylor et al., Int. Immunol. 6:579, 1994, which are hereby incorporated by reference.

The term "antibody" includes intact molecules as well as fragments thereof, such as Fab, (Fab')$_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; (Fab')$_2$, is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York, 1988, incorporated herein by reference). As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the KCNQ5 polypeptide of the invention can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), cmd tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan et al., Unit 9, Current Protocols in Immunology, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

Transgenic Animals

In another embodiment, the present invention relates to transgenic animals having cells that express KCNQ5. Such transgenic animals represent a model system for the study of KCNQ5 related disorders and the study of KCNQ5 based therapeutics.

The term "animal" here denotes all mammalian species except human. It also includes an individual animal in all stages of development, including embryonic and fetal stages. Farm animals (pigs, goats, sheep, cows, horses, rabbits and the like), rodents (such as mice), and domestic pets (for example, cats and dogs) are included within the scope of the present invention.

A "transgenic" animal is any animal containing cells that bear genetic information received, directly or indirectly, by deliberate genetic manipulation at the subcellular level, such as by microinjection or infection with recombinant virus. "Transgenic" in the present context does not encompass classical crossbreeding or in vitro fertilization, but rather denotes animals in which one or more cells receive a recombinant DNA molecule. Although it is highly preferred that this molecule be integrated within the animal's chromosomes, the present invention also contemplates the use of extrachromosomally replicating DNA sequences, such as might be engineered into yeast artificial chromosomes.

The term "transgenic animal" also includes a "germ cell line" transgenic animal. A germ cell line transgenic animal is a transgenic animal in which the genetic information has been taken up and incorporated into a germ line cell, therefore conferring the ability to transfer the information to offspring. If such offspring in fact possess some or all of that information, then they, too, are transgenic animals.

It is highly preferred that the transgenic animals of the present invention be produced by introducing into single cell embryos DNA encoding KCNQ5, in a manner such that the polynucleotides are stably integrated into the DNA of germ line cells of the mature animal and inherited in normal Mendelian fashion. Advances in technologies for embryo micromanipulation now permit introduction of heterologous DNA into fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In a preferred method, developing embryos are infected with a retrovirus containing the desired DNA, and transgenic animals produced from the infected embryo.

In a most preferred method the appropriate DNAs are coinjected into the pronucleus or cytoplasm of embryos, preferably at the single cell stage, and the embryos allowed to develop into mature transgenic animals. These techniques are well known. For instance, reviews of standard laboratory procedures for microinjection of heterologous DNAs into mammalian (mouse, pig, rabbit, sheep, goat, cow) fertilized ova include: Hogan et al., Manipulating the Mouse Embryo, Cold Spring Harbor Press, 1986; Krimpenfort et al., Bio/Technology 9:86, 1991; Palmiter et al., Cell 41:343, 1985; Kraemer et al., Genetic Manipulation of the Early Mammalian Embryo, Cold Spring Harbor Laboratory Press, 1985; Hammer et al., Nature, 315:680, 1985; Purcel et al., Science, 244:1281, 1986; Wagner et al., U.S. Pat. No. 5,175,385; Krimpenfort et al., U.S. Pat. No. 5,175,384, the respective contents of which are incorporated by reference.

The cDNA that encodes KCNQ5 can be fused in proper reading frame under the transcriptional and translational control of a vector to produce a genetic construct that is then amplified, for example, by preparation in a bacterial vector, according to conventional methods. See, for example, the standard work: Sambrook et al., Molecular Cloning: a Laboratory Manual, Cold Spring Harbor Press, 1989, the contents of which are incorporated by reference. The amplified construct is thereafter excised from the vector and purified for use in producing transgenic animals.

The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or knocked out.

The transgene to be used in the practice of the subject invention is a DNA sequence comprising a modified KCNQ5 coding sequence. In another embodiment, the transgene comprises DNA antisense to the coding sequence for KCNQ5. In a further embodiment, the transgene comprises DNA encoding an antibody or receptor peptide sequence which is able to bind to KCNQ5. Where appropriate, DNA sequences that encode proteins having KCNQ5 activity but differ in nucleic acid sequence due to the degeneracy of the genetic code may also be used herein, as may truncated forms, allelic variants and interspecies homologues. As known in the art, an allelic variant is an alternate form of a polynucleotide sequence which may have a substitution, deletion or addition of one or more nucleotides, which does not substantially alter the function of the encoded polypeptide.

The invention includes further a process for identification of a compound which compound is suitable for modification of activity of a protein having activity of KCNQ5 as mentioned before comprising a) Providing of KCNQ5 or a protein having activity of KCNQ5
b) Providing of at least one chemical compound;
c) Incubating the chemical compound according to b) with a protein according to a);
d) Measuring activity of protein according to a).

In a preferred embodiment of the invention the protein having activity of KCNQ5 as claimed from a) is provided within a host cell as aforementioned. The KCNQ5 may interact with other proteins for the purpose of this invention in a further preferred version of the invention. In particular it interacts with KCNQ3. Such a screening assay is applicable for identification of at least one chemical compound which modifies activity of KCNQ5 and which has impact on diseases of central nervous system or cardiovascular system.

Thus, in one embodiment, the invention is directed to a screening process, i.e., a method of screening for a compound that modifies the activity of KCNQ5 comprising the steps of:

(a) providing the cell culture comprising cells that express KCNQ5;
(b) providing a compound to be screened;
(c) assessing the activity of KCNQ5 in said cell culture without said compound (d) incubating said compound with said cell culture; and
(e) assessing the activity of KCNQ5 in said cell culture incubated with said compound and comparing the results of said assessment with the results of the assessment in (c); and
(f) determining whether said compound modifies said activity of KCNQ5 based on the results of (e).

The invention provides a method for identifying a compound which can modulate KCNQ5 activity. Drugs that modulate other ion channels have already had a major impact in the treatment of common diseases, as they provide the primary means to treat cardiac arrhythmias, epilepsy, hypertension, diabetes, and stroke. Furthermore, many current drugs are useful primarily because they indirectly modulate potassium channels. The method includes incubating compounds and a sample containing KCNQ5 polypeptide or polynucleotide under conditions sufficient to allow the components to interact, and measuring the effect of the compound on the expression or activity of KCNQ5. In one embodiment, the sample is a cell expressing KCNQ5 polypeptide or polynucleotide. The activity of KCNQ5 in the sample can then be compared to the KCNQ5 activity of a control sample not incubated with the compound. Alternatively, the effect of the compound on a signaling event (e.g., an ion flux) can be evaluated.

A "second messenger response" or "signaling event" means the generation of a biochemical or physiological response as a result of contacting the compound with a sample containing KCNQ5 polypeptide or polynucleotide. In general, a signaling event results in the change of a molecular characteristic or parameter of the cell. Nonlimiting examples include ion fluxes (e.g., a potassium flux), enzyme activation (e.g., a serine/threonine kinase), changes in cyclic nucleotides (e.g., cAMP, cADP, cGMP, cGDP, etc.), among others. A specific, nonlimiting example of a signaling event is the generation of a $K^+$ flux following the interaction of a compound with KCNQ5.

The effect of the compound on KCNQ5 can be measured by assessing the expression of KCNQ5 by methods well known in the art (e.g., Northern blots). Alternatively, the effect of the compound on the activity of KCNQ5 can be assessed by measuring the signaling event by any means known to one of skill in the art. In one embodiment, the electrophysiological properties of a cell expressing KCNQ5 polynucleotide or polypeptide can be measured. For example, in order to determine the effect of the compound on the activity of KCNQ5, $K^+$ selective current can be measured as whole cell current from a single cell, or in membrane patches. Single channel recordings also can be used.

Alternatively, a "physiological indicator" can be used to measure the signaling event. A "physiological indicator" is any compound in which a measurable property changes in a response to a physical parameter of the cell. Cell signaling events that occur in vivo can be of very short duration. The physiological indicators can allow measurement of the physiological parameter over the same time period that the event actually occurs, or after the event occurs (over a longer time period). One nonlimiting example of a measurable property is a change in fluorescence of an physiological indicator in response to an ion flux.

Fluorescence is one spectral property of which can be used as the means of detecting a physiological parameter of a cell. As used herein, the term "fluorescent property" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference in any one of these properties between a cell contacted with a compound of interest as compared to a control cell suffices to identify a compound which can modulate KCNQ5 activity. A measurable difference can be determined by determining the amount of any quantitative fluorescent property, e.g., the amount of fluorescence at a particular wavelength, or the integral of fluorescence over the emission spectrum. Optimally, the physiological indicator is selected to have fluorescent properties that are easily distinguishable.

A second nonlimiting example is a change in the physical location of the indicator. Movement of the indicator can be measured by means well known to one of skill in the art. For example, fluorescence activated cell sorting can be used to identify exclusion or uptake of a physiological indicator.

"Incubating" includes conditions which allow contact between the test compound and the KCNQ5. "Contacting" includes in solution and solid phase. The test compound may also be a combinatorial library for screening a plurality of compounds. Compounds identified in the method of the invention can be further evaluated, detected, cloned, sequenced, and the like, either in solution of after binding to a solid support, by any method usually applied to the detection of a specific DNA sequence, such as PCR, oligomer restriction (Saiki et al., Bio/Technology 3:1008–1012, 1985), allele-specific oligonucleotide (ASO) probe analysis (Conner et al., Proc. Natl. Acad. Sci. USA 80:278, 1983), oligonucleotide ligation assays (OLAs) (Landegren et al., Science 241:1077, 1988), and the like. Molecular techniques for DNA analysis have been reviewed (Landegren et al., Science 242:229–237. 1988).

A compound can affect KCNQ5 by either stimulating or inhibiting KCNQ5 activity. An antagonist is a compound that directly or indirectly "inhibits" an organism's ability to transport potassium by means of KCNQ5. An agonist is a compound that directly or indirectly "stimulates" an organism's ability to transport potassium by means of KCNQ5.

Agonists to KCNQ5, including those identified by the method above, are $K^+$ channel openers, which increase $K^+$ ion flux and, therefore, are useful for treating epilepsy, stroke, hypertension, asthma, Parkinson's disease, schizophrenia, anxiety, depression and neurodegeneration. While applicant does not wish to limit the scientific reasoning behind these therapeutic uses, the high degree of localization of $K^+$ channel proteins in the brain, nervous system and myocardium, $K^+$ ion flux through the $K^+$ channels of the present invention provides an ion balance and a concurrent therapeutic result.

Potential antagonists to the KCNQ5 polypeptides of the present invention include an antibody against the KCNQ5 polypeptides, or in some cases, an oligonucleotide, which bind to the KCNQ5 polypeptides and alter its conformation such that $K^+$ ions do not pass therethrough. Soluble KCNQ5 polypeptides may also be used as antagonists by administering them into circulation to bind free $K^+$ ions and, therefore, reduce their concentration in vivo.

Potential antagonists also include antisense constructs produced by antisense technology. Antisense technology controls gene expression through triple-helix formation, etc. The number of KCNQ5 channels may be reduced through antisense technology, which controls gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251:1360 (1991)), thereby preventing transcription and the production of the KCNQ5 polypeptides. The antisense RNA oligonucleotide hybridizes to the mRNA in vivo and blocks translation of the mRNA molecule into the KCNQ5 polypeptides (antisense—Okano, J. Neurochem., 56:560 (1991); Oligodeoxynucleotides as Antisense Inhibitors of Gene Expression, CRC Press, Boca Raton, Fla. (1988)). The antisense constructs can be delivered to cells by procedures known in the art such that the antisense RNA or DNA may be expressed in vivo.

Another example of a potential antagonist includes a small molecule which binds to and occupies the opening in the KCNQ5 polypeptide thereby not allowing $K^+$ ions to pass therethrough, such that normal biological activity is prevented. Examples of small molecules include but are not limited to small peptides or peptide-like molecules.

The antagonist or agonist compounds may be employed in combination with a suitable pharmaceutical carrier. Such compositions comprise a therapeutically effective amount of the compound, and a pharmaceutically acceptable carrier or excipient. Such a carrier includes but is not limited to saline, buffered saline, dextrose, water, glycerol, ethanol, and combinations thereof. The formulation should suit the mode of administration.

The screening method of the invention includes the use of a cell culture. However, it also could employ a membrane sample prepared from a cell sample. Suitable cells include any host cells containing a recombinant KCNQ5 vector of the invention. Preferably, the host cells functionally express the KCNQ5 polypeptide, but preferably have low background potassium conductance. Alternatively, cell lines expressing KCNQ5 polypeptide can be used.

In one embodiment, by employing a competition between an agonist and a compound of interest, absence of a signaling event will indicate the presence of an antagonist. These assays are well known in the literature.

The binding affinities of compounds which affect KCNQ5 can also be determined in either cells or a membrane preparation expressing KCNQ5. In these assays, a labeled ligand is employed. A number of labels have been indicated previously (e.g., radiolabels, fluorescence labels, among others) to be of use. The candidate compound is added in an appropriate buffered medium. After an incubation to ensure that binding has occurred, the surface may be washed free of any nonspecifically bound components of the assay medium, particularly any nonspecifically bound labeled ligand, and any label bound to the surface determined. The label may be quantitatively measured. By using standards, the relative binding affinity of a candidate compound can be determined.

The antibodies and polynucleotides of the invention also can be used to detect or treat a KCNQ5-associated disorder or an KCNQ5-related disorder. The term "KCNQ5-associated disorder" denotes disorders having a clinical appearance similar to or distinguishable from that produced by disorders in KCNQ5 function itself. These disorders may be understood to be caused by defects in other molecules known to participate in signaling pathways influenced by KCNQ5, or may still have no known molecule correlate. For example, it may be that only some patients with epilepsy have abnormal KCNQ5 function, while others with an identical syndrome have normal KCNQ5 function (their syndrome presumably produced by other genetic factors).

The invention can be used to determine the prognosis of a KCNQ5-associated disorder. It may also be useful in guiding choices between different treatment regimens in patients with KCNQ5-associated or -related disorders. The "prognosis" is a forecast as to the probable outcome of an attack of a disease; the prospect as to recovery from a disorder as indicated by the nature and symptoms of the case. In addition, the invention may be used to identify or treat individuals who are "at risk" of developing a KCNQ5-associated disorder. These individuals may be identified by a method of the invention for detecting the presence or absence of KCNQ5 or by any other diagnostic means, and/or may be treated by a method of the invention, prior to the actual onset of the clinical appearance of disorder. The "clinical appearance" can be any sign or symptom of the disorder.

Essentially, any disorder which is etiologically linked, as either an KCNQ5-associated or KCNQ5-related disorder, to increased expression of KCNQ5 could be considered susceptible to treatment with a KCNQ5 suppressing reagent, and any disorder which is etiologically linked, as either an KCNQ5-associated or KCNQ5-related disorder, to decreased expression of KCNQ5 could be considered susceptible to treatment with KCNQ5 activating reagents, including treatments with polynucleotides encoding KCNQ5 or the KCNQ5 polypeptide itself.

For purposes of the invention, an antibody or nucleic acid probe specific for KCNQ5 may be used to detect KCNQ5 polypeptide (using antibody) or polynucleotide (using nucleic acid probe) in subject samples such as biological fluids, cells, tissues, or nucleic acid. Any specimen containing a detectable amount of antigen or polynucleotide can be used. Examples of biological fluids of use with the invention are blood, serum, plasma, urine, mucous, and saliva. Tissue or cell samples can also be used with the subject invention. The samples can be obtained by many methods such as cellular aspiration, or by surgical removal of a biopsy sample.

The invention provides a method for detecting KCNQ5, for example, which comprises contacting an KCNQ5 antibody or nucleic acid probe with a cell suspected of expressing the KCNQ5 and detecting binding to the antibody or nucleic acid probe. The antibody reactive with the KCNQ5 or the nucleic acid probe is preferably labeled with a compound which allows detection of binding to KCNQ5. The level of the KCNQ5 in the subject cell can be compared with the level in a cell not affected by the disease process. The cell not affected by the disease process can be taken from the same subject, or can be from a control subject not affected by the disease process, or can be from a cell line. Preferably the subject is human.

When the cell component is nucleic acid, it may be necessary to amplify the nucleic acid prior to binding with the KCNQ5 specific probe. Preferably, polymerase chain reaction (PCR) is used, however, other nucleic acid amplification procedures such as ligase chain reaction (LCR), ligated activated transcription (LAT) and nucleic acid sequence-based amplification (NASBA) may be used.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Those of skill in the art will know, or can readily discern, an appropriate immunoassay format without undue experimentation.

The antibodies of the invention can be bound to many different carriers, both soluble and insoluble, and used to detect the presence of an antigen comprising the polypeptide of the invention. Examples of well-known carriers include glass, polystyrene, polypropylene, polyethylene, dextran, nylon, amylases, natural and modified celluloses, polyacrylamides, agaroses and magnetite. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific antihapten antibodies.

In using the monoclonal antibodies of the invention for the in vivo detection of antigen, the detectably labeled antibody is given a dose which is diagnostically effective. The term "diagnostically effective" means that the amount of detectably labeled monoclonal antibody is administered in sufficient quantity to enable detection of the site having the antigen comprising a polypeptide of the invention for which the monoclonal antibodies are specific.

The monoclonal antibodies or polynucleotides of the invention can be used in vitro and in vivo to monitor the course of amelioration of a KCNQ5-associated disease in a subject. Thus, for example, by measuring the increase or decrease in the number of cells expressing antigen comprising a polypeptide of the invention or changes in the concentration of such antigen present on cells or in various body fluids, it would be possible to determine whether a particular therapeutic regimen aimed at ameliorating the KCNQ5-associated disease is effective. The term "ameliorate" denotes a lessening of the detrimental effect of the KCNQ5-associated disease in the subject receiving therapy.

Therapeutic Techniques

The present invention identifies a polynucleotide sequence that can be expressed in an altered manner as compared to expression in a normal cell, therefore it is possible to design appropriate therapeutic or diagnostic techniques directed to this sequence. The antibodies and polynucleotides of the invention can be used to detect or to treat an KCNQ5-associated disorder.

Detection of elevated levels of KCNQ5 expression is accomplished by hybridization of nucleic acids isolated from a cell of interest with an KCNQ5 polynucleotide of the invention. Analysis, such as Northern Blot analysis, are utilized to quantitate expression of the KCNQ5. Other standard nucleic acid detection techniques will be known to those of skill in the art.

Treatment can include modulation of KCNQ5 gene expression and KCNQ5 activity by administration of a therapeutically effective amount of a reagent that modulates the KCNQ5. The term "modulate" envisions the suppression of expression of KCNQ5 when it is overexpressed, or augmentation of the expression of KCNQ5 when it is underexpressed. Where a disorder is associated with the decreased expression of KCNQ5, nucleic acid sequences that encode KCNQ5 can be used. Where a disorder is associated with the increased expression of KCNQ5, nucleic acid sequences that interfere with the expression of KCNQ5 can be used. This approach utilizes, for example, antisense nucleic acid, ribozymes, or triplex agents to block transcription or translation of KCNQ5 mRNA, either by masking that mRNA with an antisense nucleic acid or triplex agent, or by cleaving it with a ribozyme.

Antisense nucleic acids are DNA or RNA molecules that are complementary to at least a portion of a specific mRNA molecule (Weintraub, Scientific American 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target KCNQ5-producing cell. The use of antisense methods to inhibit the in vitro translation of genes is well known in the art (Marcus-Sakura, Anal. Biochem. 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., Antisense Res. and Dev. 1(3):227, 1991; Helene, C., Anticancer Drug Design 6(6):569), 1991.

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, J. Amer. Med. Assn. 260:3030, 1988). A major advantage of this approach is that, because they are sequence-specific, only mRNAs with particular sequences are inactivated.

Two basic types of ribozymes are tetrahymena-type (Hasselhoff, Nature 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The polypeptides and agonist and antagonist compounds which are polypeptides, may also be employed in accordance with the present invention by expression of such polypeptides in vivo, which is often referred to as "gene therapy," for the treatment of disorders which are associated with KCNQ5 protein. Such therapy would achieve its therapeutic effect by introduction of a therapeutic polynucleotide into cells having the disorder. The "therapeutic polynucleotide" may be polynucleotide sequences encoding KCNQ5, or antisense polynucleotide specific for KCNQ5, designed to treat a KCNQ5-associated disorder. Delivery of the therapeutic polynucleotide can be achieved using a recombinant expression vector such as a chimeric virus or a colloidal dispersion system. Especially preferred for therapeutic delivery of antisense sequences, or KCNQ5 polynucleotides, is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a KCNQ5 sequence of interest into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the KCNQ5 polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to Q2, PA317, and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for the therapeutic polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 .mu.m can encapsulate a substantial percentage of an aqueous buffer containing large macromolecules. RNA, DNA and intact virions can be encapsulated within the aqueous interior and be delivered to cells in a biologically active form (Fraley et al., 1981, Trends Biochem. Sci. 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino et al., Biotechniques 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

This invention involves administering to a subject a therapeutically effective dose of a pharmaceutical composition containing the compounds of the present invention and a pharmaceutically acceptable carrier. "Administering" the pharmaceutical composition of the present invention may be accomplished by any means known to the skilled artisan. By "subject" is meant any mammal, preferably a human.

The pharmaceutical compositions are preferably prepared and administered in dose units. Solid dose units are tablets, capsules and suppositories. For treatment of a patient, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention are in general administered topically, intravenously, orally or parenterally or as implants, but even rectal use is possible in principle. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer, Science 249:1527–1533, 1990, which is incorporated herein by reference.

The pharmaceutical compositions according to the invention may be administered locally or systemically. By "therapeutically effective dose" is meant the quantity of a compound according to the invention necessary to prevent, to cure or at least partially arrest the symptoms of the disorder and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al., eds., Goodman And Gilman's: The Pharmacological Bases of Therapeutics, 8th ed., Pergamon Press, 1990; and Remington's Pharmaceutical Sciences, 17th ed., Mack Publishing Co., Easton, Pa., 1990, each of which is herein incorporated by reference.

Thus the identification of KCNQ5 provides a useful tool for diagnosis, prognosis and therapeutic strategies associated with expression of KCNQ5.

This invention further refers to a method for detection of a protein as claimed having activity of KCNQ5 comprising the following steps:

a) providing biological material;
b) incubating the biological material with a compound which modifies activity of a protein having activity of KCNQ5 and if required for reference purposes with a compound which does not modify activity of KCNQ5;
c) measuring activity of a protein having activity of KCNQ5 after incubating the biological material with a chemical compound according to b).

This invention provides a method of detecting a nucleic acid sequence encoding SEQ ID NO:2 in a biological sample comprising contacting a labeled nucleic acid probe that hybridizes with said nucleic acid sequence with said biological sample under conditions wherein said probe hybridizes with said nucleic acid sequence and detecting the hybridization of said probe to said nucleic acid sequence in said sample. In this method, said nucleic acid probe may comprise a complementary sequence of SEQ ID NO:2 comprising at least 18 nucleotides in series of SEQ ID NO:2.

A method of detecting a KCNQ5 polypeptide in a biological sample comprising contacting a detectably labeled antibody that selectively binds KCNQ5 with said biological sample and detecting the binding of said antibody with said KCNQ5 polypeptide in said biological sample.

This invention also provides a method of detecting expression of a polypeptide of the present invention on the surface of a cell by detecting the presence of mRNA coding for the receptor which comprises obtaining total mRNA from the cell and contacting the mRNA so obtained with a nucleic acid probe comprising a nucleic acid molecule of at least 10 nucleotides capable of specifically hybridizing with a sequence included within the sequence of a nucleic acid molecule encoding the receptor under hybridizing conditions, detecting the presence of mRNA hybridized to the probe, and thereby detecting the expression of the receptor by the cell.

The present invention also provides a method for identifying polypeptides related to the polypeptides of the present invention. These related polypeptides may be identified by homology to a polypeptide of the present invention, by low stringency cross hybridization, or by identifying polypeptides that interact with related natural or synthetic ligands and or elicit similar behaviors after genetic or pharmacological blockade of the polypeptides of the present invention.

The present invention also contemplates the use of the genes of the present invention as a diagnostic, for example, some diseases result from inherited defective genes.

These assays may be employed to diagnose autoimmune diseases and cancer. These genes can be detected by comparing the sequences of the defective gene with that of a normal one. Subsequently, one can verify that a "mutant" gene is associated with abnormal receptor activity. In addition, one can insert mutant receptor genes into a suitable vector for expression in a functional assay system (e.g., colorimetric assay, expression on MacConkey plates, complementation experiments, in a receptor deficient strain of HEK293 cells) as yet another means to verify or identify mutations. Once "mutant" genes have been identified, one can then screen population for carriers of the "mutant" gene.

Individuals carrying mutations in the gene of the present invention may be detected at the DNA level by a variety of techniques. Nucleic acids used for diagnosis may be obtained from a patient's cells, including but not limited to such as from blood, urine, saliva, tissue biopsy and autopsy material. The genomic DNA may be used directly for detection or may be amplified enzymatically by using PCR (Saiki, et al., Nature, 324:163–166 1986) prior to analysis. RNA or cDNA may also be used for the same purpose. As an example, PCR primers complimentary to the nucleic acid of the instant invention can be used to identify and analyze mutations in the gene of the present invention. For example, deletions and insertions can be detected by a change in size of the amplified product in comparison to the normal genotype. Point mutations can be identified by hybridizing amplified DNA to radio labeled RNA of the invention or alternatively, radio labeled antisense DNA sequences of the invention. Perfectly matched sequences can be distinguished from mismatched duplexes by RNase A digestion or by differences in melting temperatures. Such a diagnostic would be particularly useful for prenatal or even neonatal testing.

Sequence differences between the reference gene and "mutants" may be revealed by the direct DNA sequencing method. In addition, cloned DNA segments may be used as probes to detect specific DNA segments. The sensitivity of this method is greatly enhanced when combined with PCR. For example, a sequence primer is used with double stranded PCR product or a single stranded template molecule generated by a modified PCR. The sequence determination is performed by conventional procedures with radio labeled nucleotide or by an automatic sequencing procedure with fluorescent-tags.

Genetic testing based on DNA sequence differences may be achieved by detection of alterations in the electrophoretic mobility of DNA fragments in gels with or without denaturing agents. Sequences changes at specific locations may also be revealed by nucleus protection assays, such RNase and S1 protection or the chemical cleavage method (e.g. Cotton, et al., PNAS, USA, 85:4397–4401 1985).

In addition, some diseases are a result of, or are characterized by changes in gene expression which can be detected by changes in the mRNA. Alternatively, the genes of the present invention can be used as a reference to identify individuals expressing a decrease of functions associated with receptors of this type.

The present invention also relates to a diagnostic assay for detecting altered levels of soluble forms of the polypeptides of the present invention in various tissues. Assays used to detect levels of the soluble polypeptides in a sample derived from a host are well known to those of skill in the art and include radioimmunoassays, competitive-binding assays, Western blot analysis and preferably as ELISA assay.

An ELISA assay initially comprises preparing an antibody specific to antigens of the polypeptides, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to the polypeptide of the present invention. Unattached reporter antibody is then washed out. Peroxidase substrates are then added to the dish and the amount of color developed in a given time period is a measurement of the amount of proteins present in a given volume of patient sample when compared against a standard curve.

Kits

Further included within this invention is a test kit comprising different parts in particular a chemical compound which is suitable of modifying the activity of KCNQ5. Such a chemical compound which is applicable as part of this test kit for modification of a protein having activity of KCNQ5 may be identified according to a method as aforementioned. Specifically, the invention refers to a kit comprising one or more containers, wherein at least one container contains a detectably labeled antibody that selectively binds a KCNQ5 polypeptide. The invention further refers to a kit comprising one or more containers, wherein at least one container contains a detectably labeled nucleic acid probe that hybridizes with a polynucleotide encoding SEQ ID NO:2.

The materials for use in the assay of the invention are ideally suited for the preparation of a kit. Such a kit may comprise a carrier means containing one or more container means such as vials, tubes, and the like, each of the container means comprising one of the separate elements to be used in the method. One of the container means may comprise a probe which is or can be detectably labeled. Such probe may be an antibody or nucleic acid sequence specific for KCNQ5, or specific fragments thereof. For example, oligonucleotide probes of the present invention can be included in a kit and used for examining the presence of KCNQ5 in a sample, as well as the quantitative (relative) degree of binding of the probe for determining the occurrence of specific strongly binding (hybridizing) sequences, thus indicating the likelihood for an subject having or predisposed to a disorder associated with KCNQ5.

The kit may also contain a container comprising a reporter-means, such as a biotin-binding protein, such as avidin or streptavidin, bound to a reporter molecule, such as an enzymatic, fluorescent, or radionucleotide label to identify the detectably labeled oligonucleotide probe.

Where the kit utilizes nucleic acid hybridization to detect the target nucleic acid, the kit may also have containers containing nucleotide(s) for amplification of the target nucleic acid sequence. When it is desirable to amplify the KCNQ5 target sequence, this can be accomplished using oligonucleotide(s) that are primers for amplification. These oligonucleotide primers are based upon identification of the flanking regions contiguous with the target nucleotide sequence.

The kit may also contain a container containing antibodies which bind to KCNQ5, or specific fragments thereof. Such antibodies can be used to distinguish the presence of KCNQ5 or the level of expression of KCNQ5 in a specimen. Where the kit utilizes antibodies to detect KCNQ5, these antibodies may be directly labeled. The kit may also contain a container containing a reporter means, such as avidin or steptavin bound to a reporter molecule such as an enzymatic, fluorescent, or radionucleotide label to identify the directly labeled antibody. Alternatively, the kit can utilizes antibodies that bind KCNQ5 that are unlabeled. The kit may then also contain a container containing a second antibody which binds to the antibody specific for KCNQ5. The second antibody can be directly labeled. The kit may also contain a container containing a reporter means, such as avidin or steptavin, bound to a reporter molecule such as an enzymatic, fluorescent, or radionucleotide label to identify the directly labeled second antibody.

A further embodiment of this invention is an isolated nucleic acid molecule encoding a fusion protein comprising a polypeptide sequence having KCNQ5 activity linked to a heterologous amino acid sequence, wherein said polypeptide sequence having KCNQ5 activity is selected from the group consisting of:
  a) a polypeptide comprising the amino acid sequence of a potassium channel KCNQ5;
  b) a polypeptide comprising the amino acid sequence of SEQ ID NO:2; and
  c) a polypeptide comprising an amino acid sequence at least 90% identical to SEQ ID NO:2.

Having generally described the invention, the same will be more readily understood by reference to the following examples, which are provided by way of illustration and are not intended to be limiting.

EXAMPLE:

Example 1

Molecular Cloning and Expression of KCNQ5

KCNQ5 a novel member of the KCNQ family of potassium channels was isolated. The gene is expressed in different regions of the brain and in skeletal muscle. When expressed in Xenopus oocytes KCNQ5 alone generates voltage-dependent, slowly activating $K^+$-selective currents that are insensitive to the $K^+$ channel blocker TEA and display a marked inward rectification at positive membrane voltages. Upon coexpression with the related KCNQ3 channel amplitude of the $K^+$ current is increased 4–5 fold. Compared to homomeric KCNQ5 currents, KCNQ3/KCNQ5 heteromeric currents also display slower activation and less inward rectification, showing that KCNQ5 combines with KCNQ3 to form functional channel proteins. The functional interaction between KCNQ5 and KCNQ3, a known protein subunit of the neuronal M-current, suggests that KCNQ5 possibly can contribute to native neuronal M-like currents.

The KCNQ5 gene was initially identified as a genomic survey sequence (BAC clone) in a homology search of GenBank (accession number AQ344243). Using this sequence a human brain cDNA library (available from Edge BioSystems) was screened. A composite full-length cDNA construct was assembled from two overlapping cDNA clones and subcloned into the Xenopus expression vector pSGEM (Villmann, C. et al.; J. Neurosci. 17, 7634–7643). The cDNA was fully sequenced on both strands using an automated DNA sequencer (ABI 310). For Xenopus oocyte expression capped cRNA was synthesized using the T7 mMessage mMachine kit (AMBION). For northern blot analysis a DIG-labeled riboprobe of 1.6 kb in length (containing mainly C-terminal sequences) was generated with the DIG RNA Labeling kit (available from ROCHE Diagnostics) according to the manufacturers instructions and hybridized to a series of human RNA blots (available from CLONTECH).

Example 2

Chromosomal Localization of KCNQ5

Fluorescence In Situ Hybridization (available from FISH, Genome Systems) analysis was performed to determine the chromosomal localization of KCNQ5. Briefly, purified DNA from the BAC clone (AQ344243) was labeled with digoxigenin dUTP by nick translation and the labeled probe was hybridized to human metaphase chromosomes derived from PHA stimulated peripheral blood lymphocytes. KCNQ5-specific signals were detected on the long arm of chromosome 6 (6q14) using fluoresceinated antidigoxigenin antibodies followed by counterstaining with DAPI and confirmed by cohybridization with a genomic clone previously mapped to 6p21.

Example 3

Electrophysiology

*Xenopus laevis* oocytes were obtained from tricaine anaesthetized animals. Ovaries were collagenase treated (1 mg/1 ml, Worthington, type II) in OR 2 solution (NaCl 82.5 mM, KCl 2 mM, $MgCl_2$ 1 mM, HEPES 5 mM, pH 7.4) for 120 min and subsequently stored in recording solution ND-96 (NaCl 96 mM, KCl 2 mM, $CaCl_2$ 1.8 mM, $MgCl_2$ 1 mM, HEPES 5 mM, pH 7.4) with additional NaPyruvate (275 mg/l), Theophylline (90 mg/l) and Gentamycin (50 mg/l) at 18° C. Oocytes were individually injected with 10 ng cRNA encoding hKCNQ5, rKCNQ3 (GenBank accession number AF087454), hKCNQ2, and hKCNQ1, respectively, or coinjected with 10 ng hKCNQ5 plus 5 ng hIsk (KCNE1), hMiRP1 (KCNE2), hMiRP2 (KCNE3), mMiRP3 (KCNE4), respectively. rKCNQ3 was cloned from λZAP cDNA library (STRATAGENE) using an DIG-labeled (ROCHE) EST-clone (GenBank accession number AA019129) as a probe. hMiRP1 and hMiRP2 were cloned from human genomic DNA, mMiRP3 from murine brain cDNA using primers derived from the published sequences (13). Standard two-electrode voltage-clamp recordings were performed at room temperature with a Turbo Tec 10CD (NPI) amplifier, an ITC-16 interface combined with Pulse software (HEKA) and Origin for data acquisition on Pentium II PC. Macroscopic currents were recorded 2–4 days after injection. All fitting procedures were based on the simplex algorithm. Student's t test was used to test for statistical significance, which was assumed if P<0.05 and indicated by*.

Example 4

Cloning and Tissue Distribution of KCNQ5

Search of the GenBank data base revealed a human BAC end sequence (AQ344243) with significant homology to the KCNQ $K^+$ channel family. The sequence information was used to isolate overlapping cDNA clones from a human brain cDNA library (Edge Biosystems) and two cDNA clones were assembled to generate a full-length cDNA clone. The initiator methionine of the cDNA was assigned to the first ATG in frame, and is preceded by a stop codon in the same frame. The full-length KCNQ5 cDNA encodes a polypeptide of 932 amino acids (FIG. 1A) with a predicted molecular mass of ≈102 kDa. Hydropathy analysis supports the topology model with six transmembrane domains. KCNQ5 shows significant homology to other KCNQ proteins, with KCNQ4 being the closest relative (65% identity). KCNQ5 is about 50% identical to KCNQ3 and KCNQ2 but only 40% to KCNQ1 (FIG. 1B). Homology is observed in particular throughout the membrane spanning regions and the conserved P-loop between transmembrane segments S5 and S6. KCNQ proteins are characterized by their very long C-terminal tails. KCNQ5 has the longest C-terminus of all KCNQ proteins followed by KCNQ2 and KCNQ3. It contains a highly conserved region the function of which is still not known, but that is frequently mutated in other KCNQ proteins. Furthermore, in a BNFC family, a frame shift mutation at the nonconserved 3' end produces a mutant KCNQ2 protein with 56 additional amino acids at its C-terminus. Surprisingly, the currents generated in oocytes by the larger mutant protein were reduced by 50% compared to the wild-type. Further, introducing a stop mutation at the very same position, which truncated the last seven amino acids, increased channel activity twofold. Together these results show that the C-terminal region of KCNQ proteins is important for channel function.

The KCNQ5 protein contains numerous potential sites for phosphorylation by PKC, but lacks a N-terminal consensus site for cAMP-dependent phosphorylation that is present in KCNQ1 and KCNQ2. KCNQ1 as well as $I_{Ks}$ currents were stimulated by PKA, whereas conflicting data have been reported concerning the effect of PKA on KCNQ2 currents.

Northern blot analyses detected 7.5 kb large KCNQ5 transcripts in human skeletal muscle and brain. In the brain transcripts are widely distributed with strongest expression in cerebral cortex, occipital pole, frontal lobe, and temporal lobe. Lower levels were detected in hippocampus and putamen. The expression pattern of KCNQ5 in the brain is very similar to that previously described for KCNQ2 and KCNQ3 that have transcripts sizes of 8.5 kb and 10.5 kb, respectively. In contrast to KCNQ2, KCNQ5 probably is absent in cerebellum.

Example 5

Expression of KCNQ5 in Xenopus Oocytes

Figure 3:
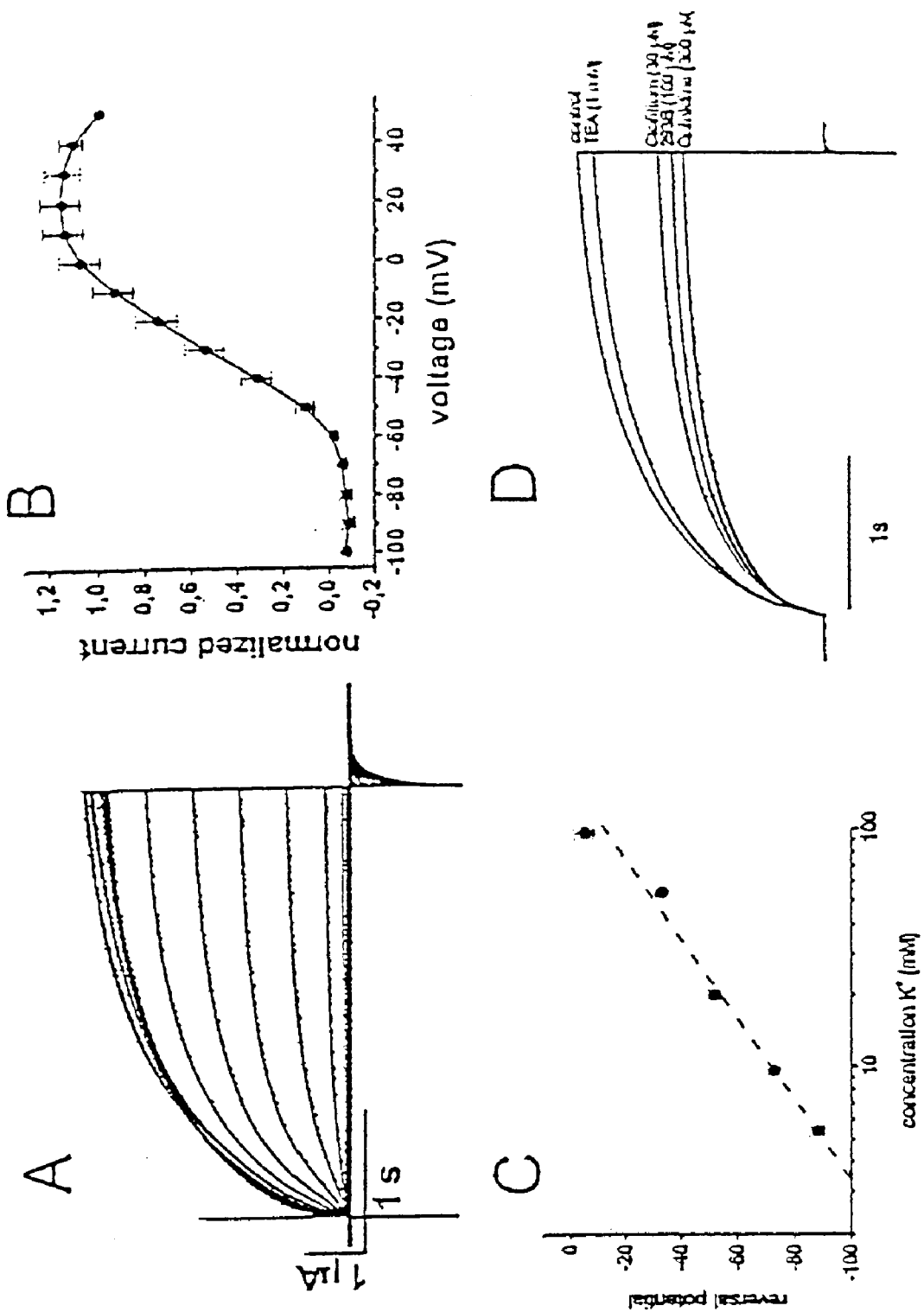
FIG. 3: Shows the functional expression of KCNQ5 in Xenopus oocytes. A, representative current traces from a KCNQ5 injected oocyte subjected to a pulse protocol that stepped the membrane potential from holding potential (−100 mV) to test pulses from −100 to +50 mV and back to holding potential. B, I-V relationships for KCNQ5 expressing oocytes (n=12) recorded using the protocol in A. C, tail current reversal potential of KCNQ 5 currents as a function of extracellular K$^+$ concentration. The dashed line is drawn according to the Nernst equation for a perfectly selective K$^+$ channel (n=5). D, effects of TEA, clofilium, quinidine, and chromanol 293 B on KCNQ 5 current. Superimposed currents were obtained during a 3 s depolarizing step from −100 mV to 0 mV, during the same experiment. Between compounds oocytes were perfused with ND 96 until complete reversal of effects (current traces are normalized to control and averaged from 5 oocytes). Error bars indicate SEM.
Figure 4:
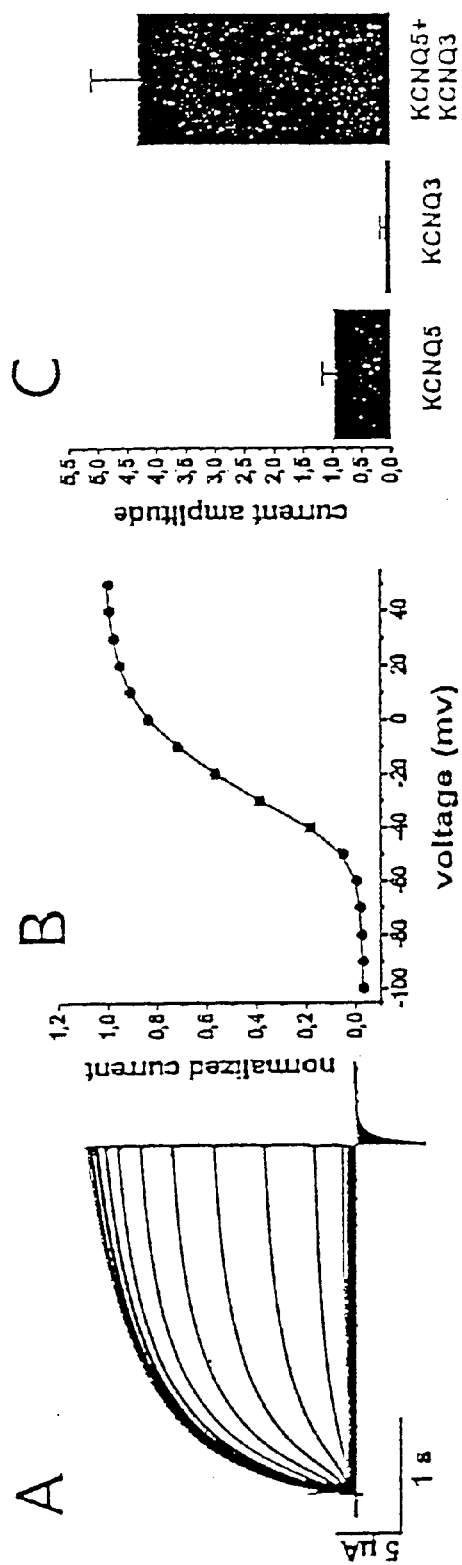
FIG. 4: Shows the functional interaction of KCNQ5 with KCNQ3. A, representative current traces recorded from an oocyte coinjected with KCNQ5 and KCNQ3 using the same protocol as in FIG. 3A. B, I-V relationships of oocytes expressing KCNQ5+KCNQ3 (n=11). C, bar graphs represent means of current amplitudes at the end of a 3s test pulse from −100 to +40 mV. Oocytes were injected with cRNA encoding KCNQ5 (n=14), KCNQ3 (n=6), or KCNQ5+KCNQ3 (n=12). Error bars indicate SEM.

The possible function of KCNQ5 as a potassium channel was addressed by electrophysiological analysis of Xenopus oocytes injected with KCNQ5 cRNA transcribed in vitro. Two to four days after injection novel currents were detected that were not observed in water-injected control oocytes. Currents activated very slowly (FIG. 3A) and were not fully activated even within 2 seconds. At lower potentials KCNQ5 currents show a delay in activation, similar to KCNQ1 currents. Activation traces above +20 mV display a cross-over phenomenon. Activation of KCNQ5 currents is generally slower than that of other KCNQ currents. However, it can be described by a biexponential function. During depolarizing pulse from −100 to +40 mV, current was activated with time constants of 116±7, and 927±51 ms (FIG. 5). Current-voltage relations of KCNQ5 currents are shown in FIG. 3B. Currents activated at depolarizing potentials positive to −60 mV and markedly inwardly rectified at potentials greater than 0 mV. Strong inward rectification only has been demonstrated for the related KCNQ3 channels. KCNQ5 deactivation was well fitted to a second order exponential function. The two components of deactivation were determined at a repolarizing voltage of −100 mV following a 3s depolarizing step to +40 mV. Time constants were 64±5 and 269±24 ms (FIG. 5). KCNQ1 tail currents display a characteristic "hook" indicative of recovery from inactivation. We did not observe such a feature at voltages between −100 and +40 mV. Additionally a double-pulse protocol was performed which is commonly used to reveal inactivation of potassium currents.

To examine the K$^+$ selectivity of KCNQ5 currents tail current reversal potentials were determined in bath solutions containing 5.4, 9.6, 20, 54 and 96 mM K$^+$. A tenfold reduction in external K$^+$ shifted the reversal potential by 58 mV (FIG. 3C), indicating that KCNQ5 is perfectly selective for K$^+$.

Pharmacological properties of KCNQ5 are shown in FIG. 3D. KCNQ5 currents were insensitive to the nonselective K$^+$ channel blocker TEA, as reported for KCNQ3. Consistently, both channel proteins contain threonine residues within the pore region at a position that determines sensitivity to blockade by TEA. In contrast, a tyrosine residue at this position is responsible for the high sensitivity of KCNQ2 to TEA. The unspecific ion channel blocker quinidine at 300 $\mu$M blocks KCNQ5 currents by 50%. Inhibitors of KCNQ1 and I$_{Ks}$ were tested at concentrations that completely or strongly block these currents. From those the chromanol 293B was the most effective one, but at 100 $\mu$M it blocked KCNQ5 currents only by 45%. In comparison, at this concentration KCNQ1 is blocked by 80%. Clofilium is a class III antiarrhythmic agent and blocks KCNQ1 with an IC$_{50}$<10 $\mu$M. At 30 $\mu$M it reduced KCNQ5 current by 40%, similar to its inhibitory effect on KCNQ3 (30% inhibition at 10$\mu$M). Clofilium produced little inhibition of KCNQ2 at 10 $\mu$M. Thus, pharmacological properties of KCNQ5 are more similar to that of KCNQ3 than to KCNQ2.

Example 6

Functional Interaction of KCNQ5 and KCNQ3

All members of the KCNQ family form functional heteromers with homologous or structurally different K$^+$ channel subunits. To investigate the possibility that KCNQ5 might also form mixed channels with a different protein subunit, we coexpressed in Xenopus oocytes KCNQ5 with other KCNQ proteins and with cDNAs encoding different KCNE polypeptides.

After coexpression with either KCNQ1 or KCNQ2, or with one of the four known KCNE peptides (KCNE1 through KCNE4), we did not observe any evidence for functional interaction of one of those proteins with KCNQ5. However, coexpression of KCNQ5 with KCNQ3 strikingly changed resulting currents. Whereas KCNQ3 alone generated only very small currents almost indistinguishable from background level in agreement with previous findings, coinjection with KCNQ5 increased currents about 4–5 times compared with KCNQ5 alone. There was no significant shift in the voltage dependency of the currents but the I-V relationship shows that KCNQ5/KCNQ3 currents were less inwardly rectifying at positive membrane potentials.

Increase in current amplitude also was accompanied by changes in gating kinetics, as shown in FIG. 5. Incorporation of KCNQ3 significantly slowed the fast component of activation but did not alter the slow component. Moreover, fast deactivation of KCNQ5/KCNQ3 currents was slowed compared to homomeric KCNQ5. In addition to a large increase in current amplitude, association of KCNQ2 and KCNQ3 also reportedly changed gating properties of the resulting heteromeric currents. Therefore, we investigated the gating kinetics of the KCNQ2/KCNQ3 current and compared it with KCNQ5/KCNQ3 (FIG. 5). In KCNQ2/KCNQ3 both fast and slow time constants of activation were slowed, as was the fast component of deactivation. Thus, while KCNQ2/KCNQ3 heteromers still activate faster than KCNQ3/KCNQ5 heteromers, deactivation kinetics of both heteromers were not significantly different.

The colocalization of KCNQ5 with KCNQ3 in various parts of the brain, the large increase in currents, and the differences in gating kinetics observed after coexpression strongly indicate that KCNQ5 can associate with KCNQ3 to form functional channels. Since KCNQ2/KCNQ3 channels are believed to constitute the molecular basis of the neuronal M-current, our results further suggest that KCNQ5 may also be a subunit of this physiologically important current. The M-current is expressed in peripheral and central neurons, but has not been described in the cerebellum. Consistently, KCNQ3 and KCNQ5 are only weakly or not expressed in this region, in contrast to KCNQ2 which curiously is strongly expressed in cerebellum.

KCNQ4 also can functionally interact with KCNQ3 to yield M-like currents, raising the possibility that heterogeneous populations of M-currents exist within the peripheral and central nervous system that probably vary in their kinetic and pharmacological properties. Heterogeneity in the molecular composition of M-like channels may even be increased by contribution of K$^+$ channels from other families.

The possibility that the KCNQ5 protein can contribute to M-currents within the brain renders the KCNQ5 gene a putative candidate for epileptic disease. By fluorescent in situ hybridization (FISH) analysis we mapped the KCNQ5 gene to chromosome 6q14. There are two loci on chromosome 6 that were linked to epileptic diseases, a known gene on 6q24, which is defect in progressive myoclonic epilepsy type 2, and an unknown gene on 6p12–p11, which is responsible for juvenile myoclonic epilepsy (EJM1). However, our mapping results exclude involvement of KCNQ5 in the latter disease. The identification of KCNQ5 makes it now possible to investigate a possible association with other forms of genetically inherited epilepsy.

For the methods used within the scope of this invention reference is made to "Current protocols of Molecular Biology; eds.: Ausubel F. M. et al.; Wiley Interscience, New York; 2000 (currently updated) " concerning Molecular Biology and to "Experimental Biochemistry; eds.: Switzer, R. L. et al. W. H. Freeman & Co 1999" concerning Biochemistry.

All above cited references, patents and patent applications are hereby incorporated by reference.

What is claimed is:

1. An isolated nucleic acid molecule encoding a potassium channel protein, KCNQ5, polypeptide comprising SEQ ID NO:2.

2. An isolated nucleic acid molecule selected from the group consisting of:
   (a) a nucleic acid molecule comprising SEQ ID NO: 1;
   (b) a nucleic acid molecule that hybridizes with a polynucleotide under conditions consisting of washing filters in 0.1×SSC, 0.1% SDS; 2 times for about 30 minutes at about 65° C. or about 5° C. below melting temperature, wherein the polynucleotide encodes a polypeptide which has substantially the same KCNQ5 activity as the polypeptide encoded by SEQ ID NO: 1;
   (c) a nucleic acid molecule encoding a polypeptide of SEQ ID NO: 2
   (d) a nucleic acid molecule that hybridizes to the nucleic acid molecule of one of (a)–(c), under conditions consisting of washing filters in 0.1×SSC, 0.1% SDS; 2 times for about 30 minutes at about 65° C. or about 5° C. below melting temperature;
   (e) a nucleic acid molecule that is degenerated from SEQ ID NO: 1, wherein said nucleic acid molecule encodes the KCNQ5 polypeptide of SEQ ID NO: 2 which has substantially the same biological activity as potassium channel protein, KCNQ5; and
   (f) a nucleic acid molecule that is complementary to the nucleic acid molecule of one of (a)–(e).

3. An expression vector comprising the isolated nucleic acid molecule of any one of claims 1 or 2.

4. The expression vector of claim 3, wherein said vector is a plasmid.

5. The expression vector of claim 3, wherein said vector is a viral vector.

6. A host cell transformed with the expression vector of claim 3.

7. The host cell of claim 6, which is a prokaryotic cell.

8. The host cell of claim 7, wherein said prokaryotic cell is a bacterium cell.

9. The host cell of claim 8, wherein said bacterium is either an *E. coli* or Bacillus spec. cell.

10. The host cell of claim 6, which is a eukaryotic cell.

11. The host cell of claim 10, wherein said eukaryotic cell is selected from the group consisting of yeast, mammalian and insect cells.

12. The host cell of claim 11, wherein said mammalian cell is selected from the group consisting of COS-, Hela and 3T3 cells.

13. A method of producing a KCNQ5 polypeptide comprising the steps of:

(a) culturing the transformed host cell of claim 6 under conditions whereby said host cell produces said polypeptide; and (b) isolating said polypeptide from said cultured host cell.

14. The host cell of claim 11, wherein said yeast cell is a *Saccharomyces cerevisiae* cell.

15. A cell culture for screening agonists and antagonists of potassium channel protein, KCNQ5, comprising cells that express KCNQ5, wherein KCNQ5 is encoded by the nucleic acid molecule of SEQ ID NO: 1.

16. The cell culture of claim 15 wherein said cells that express KCNQ5 are oocytes transformed with a nucleic acid molecule that encodes SEQ ID NO: 2.

17. A kit comprising one or more containers, wherein at least one container contains a detectably labeled nucleic acid probe that hybridizes with a polynucleotide encoding SEQ ID NO: 2 polynucleotide under conditions consisting of washing filters in 0.1×SSC, 0.1% SDS; 2 times for about 30 minutes at about 65° C. or about 5° C. below melting temperature.

* * * * *

SEQUENCE LISTING

<160> NUMBER OF SEQ ID NOS: 6

<210> SEQ ID NO 1
<211> LENGTH: 3074
<212> TYPE: DNA
<213> ORGANISM: Homo sapiens

<400> SEQUENCE: 1

```
gggcgcccg tcggccgccg gcttcctcct tgaaacccgc cggcgcacat gaggccgctg      60
ccccgccgc aggcgctggc ggcccctcg cggtgcccgt ggtgatgcca tgccccgcca     120
ccacgcggga ggagaggagg gcggcgccgc cgggctctgg gtgaagagcg gcgcagcggc     180
ggcggcggcg ggcggggggc gcttgggcag cggcatgaag gatgtggagt cgggccgggg     240
cagggtgctg ctgaactcgg cagccgccag gggcgacggc ctgctactgc tgggcacccg     300
cgcggccacg cttggtggcg gcggcggtgg cctgaggag agccgccggg gcaagcaggg     360
ggcccggatg agcctgctgg gaagccgcct ctcttacacg agtagccaga gctgccggcg     420
caacgtcaag taccggcggg tgcagaacta cctgtacaac gtgctggaga gaccccgcgg     480
ctgggcgttc atctaccacg ctttcgtttt cctccttgtc tttggttgct tgattttgtc     540
agtgttttct accatccctg agcacacaaa attggcctca agttgcctct tgatcctgga     600
gttcgtgatg attgtcgtct ttggtttgga gttcatcatt cgaatctggt ctgcgggttg     660
ctgttgtcga tatagaggat ggcaaggaag actgaggttt gctcgaaagc ccttctgtgt     720
tatagatacc attgttctta tcgcttcaat agcagttgtt tctgcaaaaa ctcagggtaa     780
tattttgcc acgtctgcac tcagaagtct ccgttccta cagatcctcc gcatggtgcg     840
catggaccga aggggaggca cttggaaatt actgggttca gtggtttatg ctcacagcaa     900
ggaattaatc acagcttggt acataggatt tttggttctt attttttcgt ctttccttgt     960
ctatctggtg gaaaaggatg ccaataaaga gttttctaca tatgcagatg ctctctggtg    1020
gggcacaatt acattgacaa ctattggcta tggagacaaa actcccctaa cttggctggg    1080
aagattgctt tctgcaggct ttgcactcct tggcatttct ttctttgcac ttcctgccgg    1140
cattcttggc tcaggttttg cattaaaagt acaagaacaa caccgccaga aacactttga    1200
gaaagaagg aacccagctg ccaacctcat tcagtgtgtt tggcgtagtt acgcagctga    1260
tgagaaatct gtttccattg caacctggaa gccacacttg aaggccttgc acacctgcag    1320
ccctaccaag aaagaacaag gggaagcatc aagcagtcag aagctaagtt taaggagcg    1380
agtgcgcatg gctagcccca ggggccagag tattaagagc cgacaagcct cagtaggtga    1440
caggaggtcc ccaagcaccg acatcacagc cgagggcagt cccaccaaag tgcagaagag    1500
ctggagcttc aacgaccgaa cccgcttccg gcccctcgctg cgcctcaaaa gttctcagcc    1560
aaaaccagtg atagatgctg acacagccct tggcactgat gatgtatatg atgaaaaagg    1620
```

-continued

| | |
|---|---|
| atgccagtgt gatgtatcag tggaagacct caccccacca cttaaaactg tcattcgagc | 1680 |
| tatcagaatt atgaaatttc atgttgcaaa acggaagttt aaggaaacat acgtccata | 1740 |
| tgatgtaaaa gatgtcattg aacaatattc tgctggtcat ctggacatgt tgtgtagaat | 1800 |
| taaaagcctt caaacacgtg ttgatcaaat tcttggaaaa gggcaaatca catcagataa | 1860 |
| gaagagccga gagaaaataa cagcagaaca tgagaccaca gacgatctca gtatgctcgg | 1920 |
| tcgggtggtc aaggttgaaa acaggtaca gtccatagaa tccaagctgg actgcctact | 1980 |
| agacatctat caacaggtcc ttcggaaagg ctctgcctca gccctcgctt tggcttcatt | 2040 |
| ccagatccca cctttgaat gtgaacagac atctgactat caaagccctg tggatagcaa | 2100 |
| agatctttcg ggttccgcac aaaacagtgg ctgcttatcc agatcaacta gtgccaacat | 2160 |
| ctcgagaggc ctgcagttca ttctgacgcc aaatgagttc agtgcccaga ctttctacgc | 2220 |
| gcttagccct actatgcaca gtcaagcaac acaggtgcca attagtcaaa gcgatggctc | 2280 |
| agcagtggca gccaccaaca ccattgcaaa ccaaataaat acggcaccca gccagcagc | 2340 |
| cccaacaact ttacagatcc cacctcctct cccagccatc aagcatctgc ccaggccaga | 2400 |
| aactctgcac cctaaccctg caggcttaca ggaaagcatt tctgacgtca ccacctgcct | 2460 |
| tgttgcctcc aaggaaaatg ttcaggttgc acagtcaaat ctcaccaagg accgttctat | 2520 |
| gaggaaaagc tttgacatgg gaggagaaac tctgttgtct gtctgtccca tggtgccgaa | 2580 |
| ggacttgggc aaatctttgt ctgtgcaaaa cctgatcagg tcgaccgagg aactgaatat | 2640 |
| acaactttca gggagtgagt caagtggctc cagaggcagc caagatttt accccaaatg | 2700 |
| gagggaatcc aaattgttta taactgatga agaggtgggt cccgaagaga cagagacaga | 2760 |
| cacttttgat gccgcaccgc agcctgccag ggaagctgcc tttgcatcag actctctaag | 2820 |
| gactggaagg tcacgatcat ctcagagcat ttgtaaggca ggagaaagta cagatgccct | 2880 |
| cagcttgcct catgtcaaac tgaaataagt tcttcatttt ctttccaggc atagcagttc | 2940 |
| tttagccata catatcattg catgaactat ttcgaaagcc cttctaaaaa gttgaaattg | 3000 |
| caagaatcgg gaagaacatg aaaggcagtt tataagcccg ttaccttta attgcatgaa | 3060 |
| aatgcatgtt tagg | 3074 |

<210> SEQ ID NO 2
<211> LENGTH: 932
<212> TYPE: PRT
<213> ORGANISM: Homo sapiens

<400> SEQUENCE: 2

Met Pro Arg His His Ala Gly Gly Glu Glu Gly Gly Ala Ala Gly Leu
1               5                   10                  15

Trp Val Lys Ser Gly Ala Ala Ala Ala Ala Gly Gly Gly Arg Leu
            20                  25                  30

Gly Ser Gly Met Lys Asp Val Glu Ser Gly Arg Gly Val Leu Leu
        35                  40                  45

Asn Ser Ala Ala Arg Gly Asp Gly Leu Leu Leu Gly Thr Arg
    50                  55                  60

Ala Ala Thr Leu Gly Gly Gly Gly Gly Leu Arg Glu Ser Arg Arg
65                  70                  75                  80

Gly Lys Gln Gly Ala Arg Met Ser Leu Leu Gly Lys Pro Leu Ser Tyr
                85                  90                  95

Thr Ser Ser Gln Ser Cys Arg Arg Asn Val Lys Tyr Arg Arg Val Gln
            100                 105                 110

```
Asn Tyr Leu Tyr Asn Val Leu Glu Arg Pro Arg Gly Trp Ala Phe Ile
            115                 120                 125
Tyr His Ala Phe Val Phe Leu Leu Val Phe Gly Cys Leu Ile Leu Ser
        130                 135                 140
Val Phe Ser Thr Ile Pro Glu His Thr Lys Leu Ala Ser Ser Cys Leu
145                 150                 155                 160
Leu Ile Leu Glu Phe Val Met Ile Val Phe Gly Leu Glu Phe Ile
            165                 170                 175
Ile Arg Ile Trp Ser Ala Gly Cys Cys Cys Arg Tyr Arg Gly Trp Gln
            180                 185                 190
Gly Arg Leu Arg Phe Ala Arg Lys Pro Phe Cys Val Ile Asp Thr Ile
            195                 200                 205
Val Leu Ile Ala Ser Ile Ala Val Val Ser Ala Lys Thr Gln Gly Asn
        210                 215                 220
Ile Phe Ala Thr Ser Ala Leu Arg Ser Leu Arg Phe Leu Gln Ile Leu
225                 230                 235                 240
Arg Met Val Arg Met Asp Arg Arg Gly Gly Thr Trp Lys Leu Leu Gly
                245                 250                 255
Ser Val Val Tyr Ala His Ser Lys Glu Leu Ile Thr Ala Trp Tyr Ile
            260                 265                 270
Gly Phe Leu Val Leu Ile Phe Ser Ser Phe Leu Val Tyr Leu Val Glu
        275                 280                 285
Lys Asp Ala Asn Lys Glu Phe Ser Thr Tyr Ala Asp Ala Leu Trp Trp
290                 295                 300
Gly Thr Ile Thr Leu Thr Thr Ile Gly Tyr Gly Asp Lys Thr Pro Leu
305                 310                 315                 320
Thr Trp Leu Gly Arg Leu Leu Ser Ala Gly Phe Ala Leu Leu Gly Ile
                325                 330                 335
Ser Phe Phe Ala Leu Pro Ala Gly Ile Leu Gly Ser Gly Phe Ala Leu
            340                 345                 350
Lys Val Gln Glu Gln His Arg Gln Lys His Phe Glu Lys Arg Arg Asn
        355                 360                 365
Pro Ala Ala Asn Leu Ile Gln Cys Val Trp Arg Ser Tyr Ala Ala Asp
370                 375                 380
Glu Lys Ser Val Ser Ile Ala Thr Trp Lys Pro His Leu Lys Ala Leu
385                 390                 395                 400
His Thr Cys Ser Pro Thr Lys Lys Glu Gln Gly Glu Ala Ser Ser Ser
                405                 410                 415
Gln Lys Leu Ser Phe Lys Glu Arg Val Arg Met Ala Ser Pro Arg Gly
            420                 425                 430
Gln Ser Ile Lys Ser Arg Gln Ala Ser Val Gly Asp Arg Arg Ser Pro
        435                 440                 445
Ser Thr Asp Ile Thr Ala Glu Gly Ser Pro Thr Lys Val Gln Lys Ser
    450                 455                 460
Trp Ser Phe Asn Asp Arg Thr Arg Phe Arg Pro Ser Leu Arg Leu Lys
465                 470                 475                 480
Ser Ser Gln Pro Lys Pro Val Ile Asp Ala Asp Thr Ala Leu Gly Thr
                485                 490                 495
Asp Asp Val Tyr Asp Glu Lys Gly Cys Gln Cys Asp Val Ser Val Glu
            500                 505                 510
Asp Leu Thr Pro Pro Leu Lys Thr Val Ile Arg Ala Ile Arg Ile Met
        515                 520                 525
Lys Phe His Val Ala Lys Arg Lys Phe Lys Glu Thr Leu Arg Pro Tyr
```

```
                530                 535                 540
Asp Val Lys Asp Val Ile Glu Gln Tyr Ser Ala Gly His Leu Asp Met
545                 550                 555                 560

Leu Cys Arg Ile Lys Ser Leu Gln Thr Arg Val Asp Gln Ile Leu Gly
                565                 570                 575

Lys Gly Gln Ile Thr Ser Asp Lys Lys Ser Arg Glu Lys Ile Thr Ala
                580                 585                 590

Glu His Glu Thr Thr Asp Asp Leu Ser Met Leu Gly Arg Val Val Lys
                595                 600                 605

Val Glu Lys Gln Val Gln Ser Ile Glu Ser Lys Leu Asp Cys Leu Leu
610                 615                 620

Asp Ile Tyr Gln Gln Val Leu Arg Lys Gly Ser Ala Ser Ala Leu Ala
625                 630                 635                 640

Leu Ala Ser Phe Gln Ile Pro Pro Phe Glu Cys Glu Gln Thr Ser Asp
                645                 650                 655

Tyr Gln Ser Pro Val Asp Ser Lys Asp Leu Ser Gly Ser Ala Gln Asn
                660                 665                 670

Ser Gly Cys Leu Ser Arg Ser Thr Ser Ala Asn Ile Ser Arg Gly Leu
                675                 680                 685

Gln Phe Ile Leu Thr Pro Asn Glu Phe Ser Ala Gln Thr Phe Tyr Ala
690                 695                 700

Leu Ser Pro Thr Met His Ser Gln Ala Thr Gln Val Pro Ile Ser Gln
705                 710                 715                 720

Ser Asp Gly Ser Ala Val Ala Thr Asn Thr Ile Ala Asn Gln Ile
                725                 730                 735

Asn Thr Ala Pro Lys Pro Ala Ala Pro Thr Thr Leu Gln Ile Pro Pro
                740                 745                 750

Pro Leu Pro Ala Ile Lys His Leu Pro Arg Pro Glu Thr Leu His Pro
                755                 760                 765

Asn Pro Ala Gly Leu Gln Glu Ser Ile Ser Asp Val Thr Thr Cys Leu
770                 775                 780

Val Ala Ser Lys Glu Asn Val Gln Val Ala Gln Ser Asn Leu Thr Lys
785                 790                 795                 800

Asp Arg Ser Met Arg Lys Ser Phe Asp Met Gly Gly Glu Thr Leu Leu
                805                 810                 815

Ser Val Cys Pro Met Val Pro Lys Asp Leu Gly Lys Ser Leu Ser Val
                820                 825                 830

Gln Asn Leu Ile Arg Ser Thr Glu Glu Leu Asn Ile Gln Leu Ser Gly
                835                 840                 845

Ser Glu Ser Ser Gly Ser Arg Gly Ser Gln Asp Phe Tyr Pro Lys Trp
850                 855                 860

Arg Glu Ser Lys Leu Phe Ile Thr Asp Glu Glu Val Gly Pro Glu Glu
865                 870                 875                 880

Thr Glu Thr Asp Thr Phe Asp Ala Ala Pro Gln Pro Ala Arg Glu Ala
                885                 890                 895

Ala Phe Ala Ser Asp Ser Leu Arg Thr Gly Arg Ser Arg Ser Ser Gln
                900                 905                 910

Ser Ile Cys Lys Ala Gly Glu Ser Thr Asp Ala Leu Ser Leu Pro His
                915                 920                 925

Val Lys Leu Lys
    930

<210> SEQ ID NO 3
```

-continued

```
<211> LENGTH: 676
<212> TYPE: PRT
<213> ORGANISM: Homo sapiens

<400> SEQUENCE: 3

Met Ala Ala Ser Ser Pro Pro Arg Ala Glu Arg Lys Arg Trp Gly
1               5                   10                  15

Trp Gly Arg Leu Pro Gly Ala Arg Arg Gly Ser Ala Gly Leu Ala Lys
            20                  25                  30

Lys Cys Pro Phe Ser Leu Glu Leu Ala Glu Gly Gly Pro Ala Gly Gly
            35                  40                  45

Ala Leu Tyr Ala Pro Ile Ala Pro Gly Ala Pro Gly Pro Ala Pro His
        50                  55                  60

Val Ser Pro Ala Ala Pro Ala Pro Pro Val Ala Ser Asp Leu Gly
65                  70                  75                  80

Pro Arg Pro Pro Val Ser Leu Asp Pro Arg Val Ser Ile Tyr Ser Thr
                85                  90                  95

Arg Arg Pro Val Leu Ala Arg Thr His Val Gln Gly Arg Val Tyr Asn
            100                 105                 110

Phe Leu Glu Arg Pro Thr Gly Trp Lys Cys Phe Val Tyr His Phe Ala
            115                 120                 125

Val Phe Leu Ile Val Leu Val Cys Leu Ile Phe Ser Val Leu Ser Thr
        130                 135                 140

Ile Glu Gln Tyr Ala Ala Leu Ala Thr Gly Thr Leu Phe Trp Met Glu
145                 150                 155                 160

Ile Val Leu Val Val Phe Phe Gly Thr Glu Tyr Val Val Arg Leu Trp
                165                 170                 175

Ser Ala Gly Cys Arg Ser Lys Tyr Val Gly Leu Trp Gly Arg Leu Arg
            180                 185                 190

Phe Ala Arg Lys Pro Ile Ser Ile Ile Asp Leu Ile Val Val Val Ala
            195                 200                 205

Ser Met Val Val Leu Cys Val Gly Ser Lys Gly Gln Val Phe Ala Thr
        210                 215                 220

Ser Ala Ile Arg Gly Ile Arg Phe Leu Gln Ile Leu Arg Met Leu His
225                 230                 235                 240

Val Asp Arg Gln Gly Gly Thr Trp Arg Leu Leu Gly Ser Val Val Phe
                245                 250                 255

Ile His Arg Gln Glu Leu Ile Thr Thr Leu Tyr Ile Gly Phe Leu Gly
            260                 265                 270

Leu Ile Phe Ser Ser Tyr Phe Val Tyr Leu Ala Glu Lys Asp Ala Val
            275                 280                 285

Asn Glu Ser Gly Arg Val Glu Phe Gly Ser Tyr Ala Asp Ala Leu Trp
        290                 295                 300

Trp Gly Val Val Thr Val Thr Thr Ile Gly Tyr Gly Asp Lys Val Pro
305                 310                 315                 320

Gln Thr Trp Val Gly Lys Thr Ile Ala Ser Cys Phe Ser Val Phe Ala
                325                 330                 335

Ile Ser Phe Phe Ala Leu Pro Ala Gly Ile Leu Gly Ser Gly Phe Ala
            340                 345                 350

Leu Lys Val Gln Gln Lys Gln Arg Gln Lys His Phe Asn Arg Gln Ile
            355                 360                 365

Pro Ala Ala Ala Ser Leu Ile Gln Thr Ala Trp Arg Cys Tyr Ala Ala
        370                 375                 380

Glu Asn Pro Asp Ser Ser Thr Trp Lys Ile Tyr Ile Arg Lys Ala Pro
```

-continued

```
                385                 390                 395                 400
Arg Ser His Thr Leu Leu Ser Pro Ser Pro Lys Pro Lys Lys Ser Val
                    405                 410                 415
Val Val Lys Lys Lys Phe Lys Leu Asp Lys Asp Asn Gly Val Thr
                420                 425                 430
Pro Gly Glu Lys Met Leu Thr Val Pro His Ile Thr Cys Asp Pro Pro
            435                 440                 445
Glu Glu Arg Arg Leu Asp His Phe Ser Val Asp Gly Tyr Asp Ser Ser
        450                 455                 460
Val Arg Lys Ser Pro Thr Leu Leu Glu Val Ser Met Pro His Phe Met
465                 470                 475                 480
Arg Thr Asn Ser Phe Ala Glu Asp Leu Asp Leu Glu Gly Glu Thr Leu
                485                 490                 495
Leu Thr Pro Ile Thr His Ile Ser Gln Leu Arg Glu His His Arg Ala
            500                 505                 510
Thr Ile Lys Val Ile Arg Arg Met Gln Tyr Phe Val Ala Lys Lys Lys
        515                 520                 525
Phe Gln Gln Ala Arg Lys Pro Tyr Asp Val Arg Asp Val Ile Glu Gln
    530                 535                 540
Tyr Ser Gln Gly His Leu Asn Leu Met Val Arg Ile Lys Glu Leu Gln
545                 550                 555                 560
Arg Arg Leu Asp Gln Ser Ile Gly Lys Pro Ser Leu Phe Ile Ser Val
                565                 570                 575
Ser Glu Lys Ser Lys Asp Arg Gly Ser Asn Thr Ile Gly Ala Arg Leu
            580                 585                 590
Asn Arg Val Glu Asp Lys Val Thr Gln Leu Asp Gln Arg Leu Ala Leu
        595                 600                 605
Ile Thr Asp Met Leu His Gln Leu Leu Ser Leu His Gly Gly Ser Thr
    610                 615                 620
Pro Gly Ser Gly Gly Pro Pro Arg Glu Gly Gly Ala His Ile Thr Gln
625                 630                 635                 640
Pro Cys Gly Ser Gly Gly Ser Val Asp Pro Glu Leu Phe Leu Pro Ser
                645                 650                 655
Asn Thr Leu Pro Thr Tyr Glu Gln Leu Thr Val Pro Arg Arg Gly Pro
            660                 665                 670
Asp Glu Gly Ser
        675

<210> SEQ ID NO 4
<211> LENGTH: 844
<212> TYPE: PRT
<213> ORGANISM: Homo sapiens

<400> SEQUENCE: 4

Met Val Gln Lys Ser Arg Asn Gly Gly Val Tyr Pro Gly Pro Ser Gly
1               5                   10                  15
Glu Lys Lys Leu Lys Val Gly Phe Val Gly Leu Asp Pro Gly Ala Pro
                20                  25                  30
Asp Ser Thr Arg Asp Gly Ala Leu Leu Ile Ala Gly Ser Glu Ala Pro
            35                  40                  45
Lys Arg Gly Ser Ile Leu Ser Lys Pro Arg Ala Gly Ala Gly Ala
        50                  55                  60
Gly Lys Pro Pro Lys Arg Asn Ala Phe Tyr Arg Lys Leu Gln Asn Phe
65                  70                  75                  80
```

-continued

```
Leu Tyr Asn Val Leu Glu Arg Pro Arg Gly Trp Ala Phe Ile Tyr His
             85                  90                  95

Ala Tyr Val Phe Leu Leu Val Phe Ser Cys Leu Val Leu Ser Val Phe
            100                 105                 110

Ser Thr Ile Lys Glu Tyr Glu Lys Ser Ser Glu Gly Ala Leu Tyr Ile
            115                 120                 125

Leu Glu Ile Val Thr Ile Val Val Phe Gly Val Glu Tyr Phe Val Arg
130                 135                 140

Ile Trp Ala Ala Gly Cys Cys Cys Arg Tyr Arg Gly Trp Arg Gly Arg
145                 150                 155                 160

Leu Lys Phe Ala Arg Lys Pro Phe Cys Val Ile Asp Ile Met Val Leu
                165                 170                 175

Ile Ala Ser Ile Ala Val Leu Ala Ala Gly Ser Gln Gly Asn Val Phe
            180                 185                 190

Ala Thr Ser Ala Leu Arg Ser Leu Arg Phe Leu Gln Ile Leu Arg Met
            195                 200                 205

Ile Arg Met Asp Arg Arg Gly Gly Thr Trp Lys Leu Leu Gly Ser Val
210                 215                 220

Val Tyr Ala His Ser Lys Glu Leu Val Thr Ala Trp Tyr Ile Gly Phe
225                 230                 235                 240

Leu Cys Leu Ile Leu Ala Ser Phe Leu Val Tyr Leu Ala Glu Lys Gly
                245                 250                 255

Glu Asn Asp His Phe Asp Thr Tyr Ala Asp Ala Leu Trp Trp Gly Leu
            260                 265                 270

Ile Thr Leu Thr Thr Ile Gly Tyr Gly Asp Lys Tyr Pro Gln Thr Trp
            275                 280                 285

Asn Gly Arg Leu Leu Ala Ala Thr Phe Thr Leu Ile Gly Val Ser Phe
290                 295                 300

Phe Ala Leu Pro Ala Gly Ile Leu Gly Ser Gly Phe Ala Leu Lys Val
305                 310                 315                 320

Gln Glu Gln His Arg Gln Lys His Phe Glu Lys Arg Arg Asn Pro Ala
                325                 330                 335

Ala Gly Leu Ile Gln Ser Ala Trp Arg Phe Tyr Ala Thr Asn Leu Ser
            340                 345                 350

Arg Thr Asp Leu His Ser Thr Trp Gln Tyr Tyr Glu Arg Thr Val Thr
            355                 360                 365

Val Pro Met Tyr Arg Leu Ile Pro Pro Leu Asn Gln Leu Glu Leu Leu
370                 375                 380

Arg Asn Leu Lys Ser Lys Ser Gly Leu Ala Phe Arg Lys Asp Pro Pro
385                 390                 395                 400

Pro Glu Pro Ser Pro Ser Gln Lys Val Ser Leu Lys Asp Arg Val Phe
                405                 410                 415

Ser Ser Pro Arg Gly Val Ala Ala Lys Gly Lys Gly Ser Pro Gln Ala
            420                 425                 430

Gln Thr Val Arg Arg Ser Pro Ser Ala Asp Gln Ser Leu Glu Asp Ser
            435                 440                 445

Pro Ser Lys Val Pro Lys Ser Trp Ser Phe Gly Asp Arg Ser Arg Ala
450                 455                 460

Arg Gln Ala Phe Arg Ile Lys Gly Ala Ala Ser Arg Gln Asn Ser Glu
465                 470                 475                 480

Glu Ala Ser Leu Pro Gly Glu Asp Ile Val Asp Asp Lys Ser Cys Pro
                485                 490                 495

Cys Glu Phe Val Thr Glu Asp Leu Thr Pro Gly Leu Lys Val Ser Ile
```

-continued

```
            500                 505                 510
Arg Ala Val Cys Val Met Arg Phe Leu Val Ser Lys Arg Lys Phe Lys
                515                 520                 525

Glu Ser Leu Arg Pro Tyr Asp Val Met Asp Val Ile Glu Gln Tyr Ser
    530                 535                 540

Ala Gly His Leu Asp Met Leu Ser Arg Ile Lys Ser Leu Gln Ser Arg
545                 550                 555                 560

Val Asp Gln Ile Val Gly Arg Gly Pro Ala Ile Thr Asp Lys Asp Arg
                565                 570                 575

Thr Lys Gly Pro Ala Glu Ala Glu Leu Pro Glu Asp Pro Ser Met Met
            580                 585                 590

Gly Arg Leu Gly Lys Val Glu Lys Gln Val Leu Ser Met Glu Lys Lys
            595                 600                 605

Leu Asp Phe Leu Val Asn Ile Tyr Met Gln Arg Met Gly Ile Pro Pro
            610                 615                 620

Thr Glu Thr Glu Ala Tyr Phe Gly Ala Lys Glu Pro Glu Pro Ala Pro
625                 630                 635                 640

Pro Tyr His Ser Pro Glu Asp Ser Arg Glu His Val Asp Arg His Gly
                645                 650                 655

Cys Ile Val Lys Ile Val Arg Ser Ser Ser Thr Gly Gln Lys Asn
                660                 665                 670

Phe Ser Ala Pro Pro Ala Ala Pro Pro Val Gln Cys Pro Pro Ser Thr
            675                 680                 685

Ser Trp Gln Pro Gln Ser His Pro Arg Gln Gly His Gly Thr Ser Pro
            690                 695                 700

Val Gly Asp His Gly Ser Leu Val Arg Ile Pro Pro Pro Ala His
705                 710                 715                 720

Glu Arg Ser Leu Ser Ala Tyr Gly Gly Asn Arg Ala Ser Met Glu
                725                 730                 735

Phe Leu Arg Gln Glu Asp Thr Pro Gly Cys Arg Pro Pro Glu Gly Thr
            740                 745                 750

Leu Arg Asp Ser Asp Thr Ser Ile Ser Ile Pro Ser Val Asp His Glu
            755                 760                 765

Glu Leu Glu Arg Ser Phe Ser Gly Phe Ser Ile Ser Gln Ser Lys Glu
            770                 775                 780

Asn Leu Asp Ala Leu Asn Ser Cys Tyr Ala Ala Val Ala Pro Cys Ala
785                 790                 795                 800

Lys Val Arg Pro Tyr Ile Ala Glu Gly Glu Ser Asp Thr Asp Ser Asp
                805                 810                 815

Leu Cys Thr Pro Cys Gly Pro Pro Arg Ser Ala Thr Gly Glu Gly
            820                 825                 830

Pro Phe Gly Asp Val Gly Trp Ala Gly Pro Arg Lys
            835                 840
```

<210> SEQ ID NO 5
<211> LENGTH: 872
<212> TYPE: PRT
<213> ORGANISM: Homo sapiens

<400> SEQUENCE: 5

```
Met Gly Leu Lys Ala Arg Arg Ala Ala Gly Ala Ala Gly Gly Gly
1               5                   10                  15

Asp Gly Gly Gly Gly Gly Gly Ala Ala Asn Pro Ala Gly Gly Asp
            20                  25                  30
```

-continued

```
Ala Ala Ala Ala Gly Asp Glu Glu Arg Lys Val Gly Leu Ala Pro Gly
         35                  40                  45

Asp Val Glu Gln Val Thr Leu Ala Leu Gly Ala Gly Ala Asp Lys Asp
         50                  55                  60

Gly Thr Leu Leu Leu Glu Gly Gly Gly Arg Asp Glu Gly Gln Arg Arg
65                   70                  75                  80

Thr Pro Gln Gly Ile Gly Leu Leu Ala Lys Thr Pro Leu Ser Arg Pro
                 85                  90                  95

Val Lys Arg Asn Asn Ala Lys Tyr Arg Arg Ile Gln Thr Leu Ile Tyr
                100                 105                 110

Asp Ala Leu Glu Arg Pro Arg Gly Trp Ala Leu Leu Tyr His Ala Leu
            115                 120                 125

Val Phe Leu Ile Val Leu Gly Cys Leu Ile Leu Ala Val Leu Thr Thr
        130                 135                 140

Phe Lys Glu Tyr Glu Thr Val Ser Gly Asp Trp Leu Leu Leu Leu Glu
145                 150                 155                 160

Thr Phe Ala Ile Phe Ile Phe Gly Ala Glu Phe Ala Leu Arg Ile Trp
                165                 170                 175

Ala Ala Gly Cys Cys Cys Arg Tyr Lys Gly Trp Arg Gly Arg Leu Lys
            180                 185                 190

Phe Ala Arg Lys Pro Leu Cys Met Leu Asp Ile Phe Val Leu Ile Ala
        195                 200                 205

Ser Val Pro Val Val Ala Val Gly Asn Gln Gly Asn Val Leu Ala Thr
210                 215                 220

Ser Leu Arg Ser Leu Arg Phe Leu Gln Ile Leu Arg Met Leu Arg Met
225                 230                 235                 240

Asp Arg Arg Gly Gly Thr Trp Lys Leu Leu Gly Ser Ala Ile Cys Ala
                245                 250                 255

His Ser Lys Glu Leu Ile Thr Ala Trp Tyr Ile Gly Phe Leu Thr Leu
            260                 265                 270

Ile Leu Ser Ser Phe Leu Val Tyr Leu Val Glu Lys Asp Val Pro Glu
        275                 280                 285

Val Asp Ala Gln Gly Glu Glu Met Lys Glu Glu Phe Glu Thr Tyr Ala
290                 295                 300

Asp Ala Leu Trp Trp Gly Leu Ile Thr Leu Ala Thr Ile Gly Tyr Gly
305                 310                 315                 320

Asp Lys Thr Pro Lys Thr Trp Glu Gly Arg Leu Ile Ala Ala Thr Phe
                325                 330                 335

Ser Leu Ile Gly Val Ser Phe Phe Ala Leu Pro Ala Gly Ile Leu Gly
            340                 345                 350

Ser Gly Leu Ala Leu Lys Val Gln Glu Gln His Arg Gln Lys His Phe
        355                 360                 365

Glu Lys Arg Arg Lys Pro Ala Ala Glu Leu Ile Gln Ala Ala Trp Arg
    370                 375                 380

Tyr Tyr Ala Thr Asn Pro Asn Arg Ile Asp Leu Val Ala Thr Trp Arg
385                 390                 395                 400

Phe Tyr Glu Ser Val Val Ser Phe Pro Phe Phe Arg Lys Glu Gln Leu
                405                 410                 415

Glu Ala Ala Ser Ser Gln Lys Leu Gly Leu Leu Asp Arg Val Arg Leu
            420                 425                 430

Ser Asn Pro Arg Gly Ser Asn Thr Lys Gly Lys Leu Phe Thr Pro Leu
        435                 440                 445

Asn Val Asp Ala Ile Glu Glu Ser Pro Ser Lys Glu Pro Lys Pro Val
```

```
              450                 455                 460
Gly Leu Asn Asn Lys Glu Arg Phe Arg Thr Ala Phe Arg Met Lys Ala
465                 470                 475                 480
Tyr Ala Phe Trp Gln Ser Ser Glu Asp Ala Gly Thr Gly Asp Pro Met
                    485                 490                 495
Ala Glu Asp Arg Gly Tyr Gly Asn Asp Phe Pro Ile Glu Asp Met Ile
                500                 505                 510
Pro Thr Leu Lys Ala Ala Ile Arg Ala Val Arg Ile Leu Gln Phe Arg
                515                 520                 525
Leu Tyr Lys Lys Lys Phe Lys Glu Thr Leu Arg Pro Tyr Asp Val Lys
530                 535                 540
Asp Val Ile Glu Gln Tyr Ser Ala Gly His Leu Asp Met Leu Ser Arg
545                 550                 555                 560
Ile Lys Tyr Leu Gln Thr Arg Ile Asp Met Ile Phe Thr Pro Gly Pro
                565                 570                 575
Pro Ser Thr Pro Lys His Lys Lys Ser Gln Lys Gly Ser Ala Phe Thr
                580                 585                 590
Phe Pro Ser Gln Gln Ser Pro Arg Asn Glu Pro Tyr Val Ala Arg Pro
        595                 600                 605
Ser Thr Ser Glu Ile Glu Asp Gln Ser Met Met Gly Lys Phe Val Lys
        610                 615                 620
Val Glu Arg Gln Val Gln Asp Met Gly Lys Lys Leu Asp Phe Leu Val
625                 630                 635                 640
Asp Met His Met Gln His Met Glu Arg Leu Gln Val Gln Val Thr Glu
                    645                 650                 655
Tyr Tyr Pro Thr Lys Gly Thr Ser Ser Pro Ala Glu Ala Glu Lys Lys
                660                 665                 670
Glu Asp Asn Arg Tyr Ser Asp Leu Lys Thr Ile Ile Cys Asn Tyr Ser
            675                 680                 685
Glu Thr Gly Pro Pro Glu Pro Pro Tyr Ser Phe His Gln Val Thr Ile
        690                 695                 700
Asp Lys Val Ser Pro Tyr Gly Phe Phe Ala His Asp Pro Val Asn Leu
705                 710                 715                 720
Pro Arg Gly Gly Pro Ser Ser Gly Lys Val Gln Ala Thr Pro Pro Ser
                725                 730                 735
Ser Ala Thr Thr Tyr Val Glu Arg Pro Thr Val Leu Pro Ile Leu Thr
                740                 745                 750
Leu Leu Asp Ser Arg Val Ser Cys His Ser Gln Ala Asp Leu Gln Gly
                755                 760                 765
Pro Tyr Ser Asp Arg Ile Ser Pro Arg Gln Arg Ser Ile Thr Arg
        770                 775                 780
Asp Ser Asp Thr Pro Leu Ser Leu Met Ser Val Asn His Glu Glu Leu
785                 790                 795                 800
Glu Arg Ser Pro Ser Gly Phe Ser Ile Ser Gln Asp Arg Asp Tyr
                805                 810                 815
Val Phe Gly Pro Asn Gly Gly Ser Ser Trp Met Arg Glu Lys Arg Tyr
                820                 825                 830
Leu Ala Glu Gly Glu Thr Asp Thr Asp Thr Asp Pro Phe Thr Pro Ser
            835                 840                 845
Gly Ser Met Pro Leu Ser Ser Thr Gly Asp Gly Ile Ser Asp Ser Val
        850                 855                 860
Trp Thr Pro Ser Asn Lys Pro Ile
865                 870
```

```
<210> SEQ ID NO 6
<211> LENGTH: 696
<212> TYPE: PRT
<213> ORGANISM: Homo sapiens

<400> SEQUENCE: 6

Met Ala Glu Ala Pro Pro Arg Arg Leu Gly Leu Gly Pro Pro Gly
 1               5                  10                  15

Asp Ala Pro Arg Ala Glu Leu Val Ala Leu Thr Ala Val Gln Ser Glu
                 20                  25                  30

Gln Gly Glu Ala Gly Gly Gly Ser Pro Arg Arg Leu Gly Leu Leu
             35                  40                  45

Gly Ser Pro Leu Pro Pro Gly Ala Pro Leu Pro Gly Pro Gly Ser Gly
     50                  55                  60

Ser Gly Ser Ala Cys Gly Gln Arg Ser Ala Ala His Lys Arg Tyr
65               70                  75                  80

Arg Arg Leu Gln Asn Trp Val Tyr Asn Val Leu Glu Arg Pro Arg Gly
                 85                  90                  95

Trp Ala Phe Val Tyr His Val Phe Ile Phe Leu Leu Val Phe Ser Cys
                100                 105                 110

Leu Val Leu Ser Val Leu Ser Thr Ile Gln Glu His Gln Glu Leu Ala
            115                 120                 125

Asn Glu Cys Leu Leu Ile Leu Glu Phe Val Met Ile Val Val Phe Gly
130                 135                 140

Leu Glu Tyr Ile Val Arg Val Trp Ser Ala Gly Cys Cys Cys Arg Tyr
145                 150                 155                 160

Arg Gly Trp Gln Gly Arg Phe Arg Phe Ala Arg Lys Pro Phe Cys Val
                165                 170                 175

Ile Asp Phe Ile Val Phe Val Ala Ser Val Ala Val Ile Ala Ala Gly
            180                 185                 190

Thr Gln Gly Asn Ile Phe Ala Thr Ser Ala Leu Arg Ser Met Arg Phe
            195                 200                 205

Leu Gln Ile Leu Arg Met Val Arg Met Asp Arg Arg Gly Gly Thr Trp
210                 215                 220

Lys Leu Leu Gly Ser Val Val Tyr Ala His Ser Lys Glu Leu Ile Thr
225                 230                 235                 240

Ala Trp Tyr Ile Gly Phe Leu Val Leu Ile Phe Ala Ser Phe Leu Val
                245                 250                 255

Tyr Leu Ala Glu Lys Asp Ala Asn Ser Asp Phe Ser Ser Tyr Ala Asp
            260                 265                 270

Ser Leu Trp Trp Gly Thr Ile Thr Leu Thr Thr Ile Gly Tyr Gly Asp
        275                 280                 285

Lys Thr Pro His Thr Trp Leu Gly Arg Val Leu Ala Ala Gly Phe Ala
    290                 295                 300

Leu Leu Gly Ile Ser Phe Phe Ala Leu Pro Ala Gly Ile Leu Gly Ser
305                 310                 315                 320

Gly Phe Ala Leu Lys Val Gln Glu Gln His Arg Gln Lys His Phe Glu
                325                 330                 335

Lys Arg Arg Met Pro Ala Ala Asn Leu Ile Gln Ala Ala Trp Arg Leu
            340                 345                 350

Tyr Ser Thr Asp Met Ser Arg Ala Tyr Leu Thr Ala Thr Trp Tyr Tyr
        355                 360                 365

Tyr Asp Ser Ile Leu Pro Ser Phe Arg Glu Leu Ala Leu Leu Phe Glu
```

-continued

```
            370                 375                 380
His Val Gln Arg Ala Arg Asn Gly Gly Leu Arg Pro Leu Glu Val Arg
385                 390                 395                 400

Arg Ala Pro Val Pro Asp Gly Ala Pro Ser Arg Tyr Pro Pro Val Ala
                405                 410                 415

Thr Cys His Arg Pro Gly Ser Thr Ser Phe Cys Pro Gly Glu Ser Ser
                420                 425                 430

Arg Met Gly Ile Lys Asp Arg Ile Arg Met Gly Ser Ser Gln Arg Arg
            435                 440                 445

Thr Gly Pro Ser Lys Gln Gln Leu Ala Pro Pro Thr Met Pro Thr Ser
    450                 455                 460

Pro Ser Ser Glu Gln Val Gly Glu Ala Thr Ser Pro Thr Lys Val Gln
465                 470                 475                 480

Lys Ser Trp Ser Phe Asn Asp Arg Thr Arg Phe Arg Ala Ser Leu Arg
                485                 490                 495

Leu Lys Pro Arg Thr Ser Ala Glu Asp Ala Pro Ser Glu Glu Val Ala
                500                 505                 510

Glu Glu Lys Ser Tyr Gln Cys Glu Leu Thr Val Asp Asp Ile Met Pro
            515                 520                 525

Ala Val Lys Thr Val Ile Arg Ser Ile Arg Ile Leu Lys Phe Leu Val
    530                 535                 540

Ala Lys Arg Lys Phe Lys Glu Thr Leu Arg Pro Tyr Asp Val Lys Asp
545                 550                 555                 560

Val Ile Glu Gln Tyr Ser Ala Gly His Leu Asp Met Leu Gly Arg Ile
                565                 570                 575

Lys Ser Leu Gln Thr Arg Val Asp Gln Ile Val Gly Arg Gly Pro Gly
                580                 585                 590

Asp Arg Lys Ala Arg Glu Lys Gly Asp Lys Gly Pro Ser Asp Ala Glu
            595                 600                 605

Val Val Asp Glu Ile Ser Met Met Gly Arg Val Val Lys Val Glu Lys
    610                 615                 620

Gln Val Gln Ser Ile Glu His Lys Leu Asp Leu Leu Leu Gly Phe Tyr
625                 630                 635                 640

Ser Arg Cys Leu Arg Ser Gly Thr Ser Ala Ser Leu Gly Ala Val Gln
                645                 650                 655

Val Pro Leu Phe Asp Pro Asp Ile Thr Ser Asp Tyr His Ser Pro Val
                660                 665                 670

Asp His Glu Asp Ile Ser Val Ser Ala Gln Thr Leu Ser Ile Ser Arg
            675                 680                 685

Ser Val Ser Thr Asn Met Asp Gly
    690                 695
```